(12) United States Patent
Steiner et al.

(10) Patent No.: US 7,524,866 B2
(45) Date of Patent: *Apr. 28, 2009

(54) PREVENTION AND TREATMENT OF ANDROGEN—DEPRIVATION INDUCED OSTEOPOROSIS

(75) Inventors: Mitchell S. Steiner, Germantown, TN (US); Sharan Raghow, Collierville, TN (US); Karen A. Veverka, Cordova, TN (US)

(73) Assignee: GTx, Inc., Memphis, TN (US)

( * ) Notice: Subject to any disclaimer, the term of this patent is extended or adjusted under 35 U.S.C. 154(b) by 657 days.

This patent is subject to a terminal disclaimer.

(21) Appl. No.: 10/778,334

(22) Filed: Feb. 17, 2004

(65) Prior Publication Data

US 2004/0235806 A1 Nov. 25, 2004

Related U.S. Application Data

(63) Continuation-in-part of application No. 10/609,684, filed on Jul. 1, 2003, now abandoned, which is a continuation-in-part of application No. 10/305,363, filed on Nov. 27, 2002, now Pat. No. 6,899,888.

(60) Provisional application No. 60/333,734, filed on Nov. 29, 2001.

(51) Int. Cl.
*A61K 31/445* (2006.01)
*A61K 31/38* (2006.01)
*A61K 31/135* (2006.01)

(52) U.S. Cl. ......................... 514/324; 514/443; 514/648

(58) Field of Classification Search .................. 514/324, 514/443, 648
See application file for complete search history.

(56) References Cited

U.S. PATENT DOCUMENTS

4,729,999 A 3/1988 Young et al.

(Continued)

FOREIGN PATENT DOCUMENTS

EP 1 004 306 5/2001

(Continued)

OTHER PUBLICATIONS

Beratti et al., "Background to and Management of Treatment-Related Bone Loss in Prostate Cancer", Therapy in Practice, Drugs-Aging, vol. 19, No. 12, pp. 899-910.*

(Continued)

*Primary Examiner*—Raymond J Henley, III
(74) *Attorney, Agent, or Firm*—Pearl Cohen Zedek Latzer, LLP; Mark S. Cohen

(57) ABSTRACT

This invention provides: 1) a method of treating androgen-deprivation induced osteoporosis and/or bone fractures and/or loss of Bone Mineral Density (BMD) in a male subject suffering from prostate cancer; 2) a method of preventing androgen-deprivation induced osteoporosis and/or bone fractures and/or loss of Bone Mineral Density (BMD) in a male subject suffering from prostate cancer; 3) a method of suppressing or inhibiting androgen-deprivation induced osteoporosis and/or bone fractures and/or loss of BMD in a male subject suffering from prostate cancer; and 4) a method of reducing the risk of developing androgen-deprivation induced osteoporosis and/or bone fractures and/or loss of BMD in a male subject suffering from prostate cancer, by administering to the subject a pharmaceutical composition comprising an anti-estrogen agent and/or its analog, derivative, isomer, metabolite, pharmaceutically acceptable salt, pharmaceutical product, hydrate, N-oxide, or any combination thereof.

63 Claims, 5 Drawing Sheets

U.S. PATENT DOCUMENTS

| | | | |
|---|---|---|---|
| 5,610,150 | A | 3/1997 | Labrie et al. |
| 6,017,964 | A | 1/2000 | MacLean et al. |
| 6,153,622 | A | 11/2000 | Cameron et al. |
| 6,262,098 | B1 | 7/2001 | Huebner et al. |
| 6,265,448 | B1 | 7/2001 | Steiner et al. |
| 6,410,043 | B1 | 6/2002 | Steiner et al. |
| 6,413,533 | B1 | 7/2002 | Steiner et al. |
| 6,413,534 | B1 | 7/2002 | Steiner et al. |
| 6,413,535 | B1 | 7/2002 | Steiner et al. |
| 6,632,447 | B1 | 10/2003 | Steiner et al. |
| 6,838,584 | B2 | 1/2005 | Blizzard et al. |
| 6,899,888 | B2 * | 5/2005 | Steiner et al. ............... 424/423 |
| 2004/0142973 | A1 | 7/2004 | Castle |

FOREIGN PATENT DOCUMENTS

| | | |
|---|---|---|
| WO | WO 99/65488 | 12/1999 |
| WO | WO 00/07576 | 2/2000 |
| WO | WO 01/49673 | 7/2001 |
| WO | WO 01/89515 | 11/2001 |
| WO | WO 01/91744 | 12/2001 |
| WO | WO 02/02099 | 1/2002 |
| WO | WO 02 053522 | 7/2002 |
| WO | WO 03 043606 | 5/2003 |

OTHER PUBLICATIONS

Buelke-Sam J. et al. "The Selective Estrogen Receptor Modulator, Raloxifene: An Overview Of NonClinical Pharmacology and Reproductive And Developmental Testing", Reprod Toxicol May-Jun. 1998; 12(3):217-21.

Goodson Max J. "Dental Applications" vol. 11, Chapter 6, date not available.

Horwitz Eric M. et al "Subset Analysis of RTOG 85031 and 86-10 Indicates An Advantage For Long-Term vs. Short-Terms Adjuvant Hormones For Patients With Locally Advanced Nonmetastatic Prostate Cancer Treated with Radiation Therapy", Int. J. Radiation Oncology Biol. Phys. vol. 49, No. 4 pp. 947-956, 2001, Elsevier Science Inc.

Jordan Craig V. "Antiestrogenic Action of Raloxifene and Tamoxifen: Today and Tomorrow" Journal of National Cancer Institute, vol. 90, No. 13, Jul. 1, 1998.

Labrie, et al (1997) "Method and Treatment of androgen-related diseases" Biotechnology Advances vol. 15 No. 3-4;778-779.

Messing Edward M. et al "Immediate Hormonal Therapy Compared With Observation After Radical Prostatectomy and Pelvic Lymphadenectomy in Men With Node-Positive Prostate Cancer" The New England Journal of Medicine, 1999 vol. 341, No. 24.

Newling Don W.W. "Early Versus Late Androgen Deprivation Therapy in Metastatic Disease", Elsevier Science Inc, Urology 58 (supplement 2A), Aug. 2001.

O'Brien Frank M. et al "Insulin-like Growth Fact I and Prostate Cancer", 2001 Elsevier Science Inc, Urology 58:1-7, 2001.

Stege Reinhard et al. "Potential Side-Effects of Endocrine Treatment of Long Duration in Prostate Cancer" The Prostate Supplement 10:38-42, 2000.

Broulik, et al (2000) "Tamoxifen Prevents Bone Loss in Casterated Male Mice." Horm Metab Res 181-184.

Labrie, et al (1997) "Method and treatment of androgen-related diseases" Biotechnology Advances. vol. 15 No. 3-4. 778-779.

Moyad, et al (2002) "Complementary/alternative therapies for reducing hot flashes in prostate cancer patients: reevaluating the existing indirect data from studies of breast cancer and postmenopausal women."Urology. 59(4 Suppl 1):20-33.

* cited by examiner

Figure 1. Effect of Toremifene on C-telopeptide of rat collagen I (RatLaps ELISA)

(p<0.001 Orx and each treatment group vs. sham)

PREVENTION AND TREATMENT OF ANDROGEN—DEPRIVATION INDUCED OSTEOPOROSIS

CROSS REFERENCE TO RELATED APPLICATION

This application is a continuation-in-part of U.S. patent application Ser. No. 10/609,684, filed Jul. 1, 2003, now abandoned, which is a continuation-in-part of U.S. patent application Ser. No. 10/305,363, filed Nov. 27, 2002, now U.S. Pat. No. 6,899,888, and claims priority of U.S. Provisional Patent Application Ser. No. 60/333,734, filed Nov. 29, 2001, all of which are hereby incorporated in their entirety by reference herein.

FIELD OF INVENTION

This invention relates to reducing the incidence of, inhibiting, suppressing, preventing and treating androgen-deprivation induced osteoporosis and/or bone fractures and/or loss of bone mineral density (BMD) in men suffering from prostate cancer. More particularly, this invention relates to a method of treating, preventing, suppressing, inhibiting, or reducing the risk of developing androgen-deprivation induced osteoporosis and/or bone fractures and/or loss of BMD in men suffering from prostate cancer, comprising administering to a male subject suffering from prostate cancer an anti-estrogen agent and/or its analog, derivative, isomer, metabolite, pharmaceutically acceptable salt, pharmaceutical product, hydrate, N-oxide, or any combination thereof.

BACKGROUND OF THE INVENTION

It is well established that the bone mineral density. of males decrease with age. Decreased amounts of bone mineral content and density correlate with decreased bone strength and predispose to fracture. The molecular mechanisms underlying the pleiotropic effects of sex hormones in non-reproductive tissues are only beginning to be understood, but it is clear that physiologic concentrations of androgens and estrogens play an important role in maintaining bone homeostasis throughout the life cycle. Consequently, when androgen or estrogen deprivation occurs, there is a resultant increase in the rate of bone remodeling that tilts the balance of resorption and formation in the favor of resorption, contributing to an overall loss of bone mass. In males, the natural decline in sex hormones at maturity (direct decline in androgens as well as lower levels of estrogens derived from peripheral aromatization of androgens) is associated with the frailty of bones. This effect is also observed in males who have been castrated.

Prostate cancer is one of the most frequently diagnosed noncutaneous cancers among men in the United States. One of the approaches to the treatment of prostate cancer is by androgen deprivation. The male sex hormone, testosterone, stimulates the growth of cancerous pro static cells and, therefore, is the primary fuel for the growth of prostate cancer. The goal of androgen deprivation is to decrease the stimulation by testosterone of the cancerous prostatic cells. Testosterone normally is produced by the testes in response to stimulation from a hormonal signal called luteinizing hormone (LH), which in turn is stimulated by luteinizing-hormone releasing hormone (LH-RH). Androgen deprivation is accomplished either surgically by bilateral orchidectomy or chemically by LH-RH agonists (LHRH) with or without nonsteroidal anti-androgens.

Current studies suggest that early androgen deprivation in patients with micrometastatic disease may indeed prolong survival [Messing E M, et al (1999), N Engl J Med 34, 1781-1788; Newling (2001), Urology 58(Suppl 2A), 50-55]. Moreover, androgen deprivation is being employed in numerous new clinical settings, including neoadjuvant therapy prior to radical prostatectomy, long-term adjuvant therapy for patients at high risk for recurrence following radiation or surgery, neoadjuvant therapy for radiation, and treatment of biochemical recurrence following radiation or surgery [Carroll, et al (2001), Urology 58, 1-4; Horwitz E M, et al (2001), Int J Radiat Oncol Biol Phy Mar 15;49(4), 947-56]. Thus, more prostate cancer patients have become candidates for and are being treated by androgen ablation. Moreover, these prostate cancer patients are being treated earlier and longer than in the past, which in some cases may be as long as 10 or more years of androgen deprivation therapy.

Unfortunately, androgen deprivation therapy is fraught with significant side effects, including hot flashes, gynecomastia, osteoporosis, decreased lean muscle mass, depression and other mood changes, loss of libido, and erectile dysfunction [Stege R (2000), Prostate Suppl 10,38-42]. Consequently, complications of androgen blockade now contribute significantly to the morbidity, and in some cases the mortality, of men suffering from prostate cancer.

Given that more patients today are being treated by long-term androgen deprivation, osteoporosis has become a clinically important side effect in men suffering from prostate cancer undergoing androgen deprivation. Loss of bone mineral density (BMD) occurs in the majority of patients being treated by androgen deprivation by 6 months. New innovative approaches are urgently needed at both the basic science and clinical levels to decrease the incidence of androgen-deprivation induced osteoporosis in men suffering from prostate cancer.

SUMMARY OF THE INVENTION

This invention relates to a method of treating androgen-deprivation induced osteoporosis in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof.

This invention relates to a method of preventing androgen-deprivation induced osteoporosis in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof.

This invention relates to a method of suppressing or inhibiting androgen-deprivation induced osteoporosis in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof.

This invention relates to a method of reducing the risk of developing androgen-deprivation induced osteoporosis in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof.

This invention relates to a method of treating androgen-deprivation induced loss of BMD in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof.

This invention relates to a method of preventing androgen-deprivation induced loss of BMD in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof.

This invention relates to a method of suppressing or inhibiting androgen-deprivation induced loss of BMD in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof.

This invention relates to a method of reducing the risk of developing androgen-deprivation induced loss of BMD in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof.

This invention relates to a method of treating androgen-deprivation induced bone fractures in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof.

This invention relates to a method of preventing androgen-deprivation induced bone fractures in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof.

This invention relates to a method of suppressing or inhibiting androgen-deprivation induced bone fractures in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof.

This invention relates to a method of reducing the risk of developing androgen-deprivation induced bone fractures in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof.

In one embodiment the anti-estrogen is a selective estrogen receptor modulator (SERM). In another embodiment, the anti-estrogen is a triphenylethylene. In another embodiment, the anti-estrogen is Toremifene.

In one embodiment, the anti-estrogen is administered at a daily dosage of about 20 mg. In another embodiment, the anti-estrogen is administered at a daily dosage of about 40 mg. In another embodiment, the anti-estrogen is administered at a daily dosage of about 60 mg. In another embodiment, the anti-estrogen is administered at a daily dosage of about 80 mg.

In one embodiment, the anti-estrogen is Toremifene, which is administered at a daily dosage of about 20 mg. In another embodiment, the anti-estrogen is Toremifene, which is administered at a daily dosage of about 40 mg. In another embodiment, the anti-estrogen is Toremifene, which is administered at a daily dosage of about 60 mg. In another embodiment, the anti-estrogen is Toremifene, which is administered at a daily dosage of about 80 mg.

The present invention provides a safe and effective method for treating, preventing, suppressing, inhibiting or reducing the risk of developing androgen-deprivation induced osteoporosis and/or loss of BMD and is particularly useful for treating male subjects suffering from prostate cancer having an elevated risk of developing androgen-deprivation induced osteoporosis and/or loss of BMD.

BRIEF DESCRIPTION OF THE FIGURES

The present invention will be understood and appreciated more fully from the following detailed description taken in conjunction with the appended figures which depict.

DETAILED DESCRIPTION OF THE INVENTION

Figure 1:
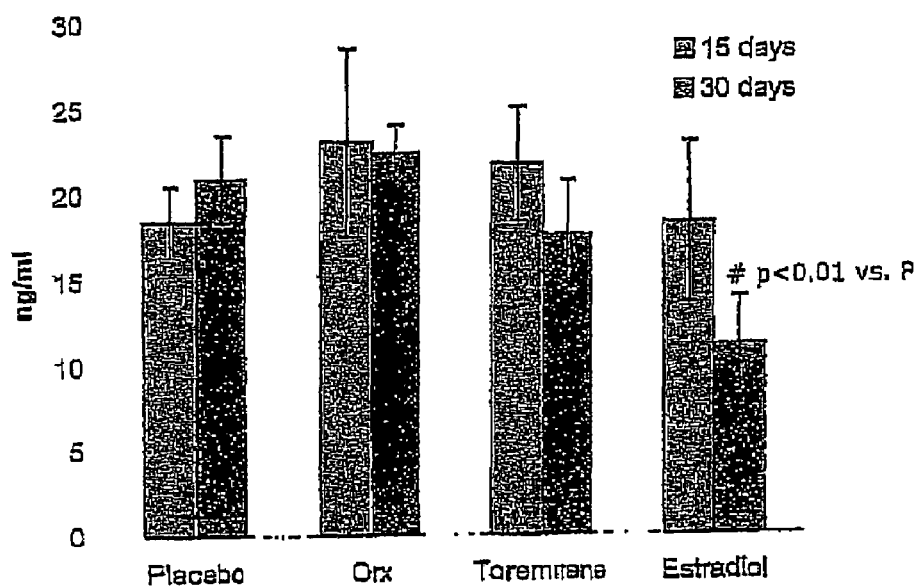
FIG. 1: Effect of Toremifene on C-telopeptide of rat collagen I (RatLaps ELISA).

This invention provides: 1) a method of treating androgen-deprivation induced osteoporosis in a male subject suffering from prostate cancer; 2) a method of preventing androgen-deprivation induced osteoporosis in a male subject suffering from prostate cancer; 3) a method of suppressing or inhibiting androgen-deprivation induced osteoporosis in a male subject suffering from prostate cancer; 4) a method of reducing the risk of developing androgen-deprivation induced osteoporosis in a male subject suffering from prostate cancer; 5) a method of treating androgen-deprivation induced loss of BMD in a male subject suffering from prostate cancer; 6) a method of preventing androgen-deprivation induced loss of BMD in a male subject suffering from prostate cancer; 7) a method of suppressing or inhibiting androgen-deprivation induced loss of BMD in a male subject suffering from prostate cancer; 8) a method of reducing the risk of developing androgen-deprivation induced loss of BMD in a male subject suffering from prostate cancer; 9) a method of treating androgen-deprivation induced bone fractures in a male subject suffering from prostate cancer; 10) a method of preventing androgen-deprivation induced bone fractures in a male subject suffering from prostate cancer; 11) a method of suppressing or inhibiting androgen-deprivation induced bone fractures in a male subject suffering from prostate cancer; 12) a method of reducing the risk of developing androgen-deprivation induced bone fractures in a male subject suffering from prostate cancer by administering to the subject an anti-estrogen agent and/or its analog, derivative, isomer, metabolite, pharmaceutically acceptable salt, pharmaceutical product, hydrate, N-oxide, or any combination thereof.

As provided herein, the results demonstrate that administration of an anti-estrogen, such as, for example, Toremifene, at a daily dosage of from about 20 mg to about 80 mg, is bone sparing. This is determined by measuring the levels of bone-specific serum markers that indicate bone resorption and formation. Further, this invention demonstrates that an anti-estrogen, such as, for example, Toremifene (and/or 17-β-Estradiol), increases bone mineral density.

Toremifene is an example of a triphenylalkylene compound described in U.S. Pat. Nos. 4,696,949 and 5,491,173 to Toivola et al., the disclosures of which are incorporated herein by reference. The parenteral and topical administration to mammalian subjects of formulations containing Toremifene is described in U.S. Pat. No. 5,571,534 to Jalonen et al. and in U.S. Pat. No. 5,605,700 to DeGregorio et al., the disclosures of which are incorporated herein by reference.

In one embodiment, the anti-estrogen that treats, prevents, suppresses, inhibits or reduces the risk of developing androgen-deprivation induced osteoporosis and/or loss of BMD is a selective estrogen receptor modulator (SERM) and/or its analog, derivative, isomer, metabolite, pharmaceutically acceptable salt, pharmaceutical product, hydrate, N-oxide, or any combination thereof.

In one embodiment, the SERMs that are encompassed by the present invention include, but are not limited to, the following embodiments: triphenylalkylenes such as triphenylethylenes, which include Tamoxifen, Droloxifene, Toremifene, Idoxifene, Clomiphene, Enclomiphene and Zuclomiphene; benzothiphene derivatives such as Raloxifene and LY 353381; benzopyran derivatives such as EM 800 (SCH 57050) and its metabolite EM 652; naphthalene derivatives such as Lasofoxifene (CP 336,156); chromans such as Levormeloxifene or their analogs, derivatives, isomers, or metabolites thereof, or their pharmaceutically acceptable salts, esters, N-oxides, or mixtures thereof.

As contemplated herein, other embodiments of anti-estrogens that are encompassed by the present invention include but are in no way limited to the following embodiments: Cycladiene, Merck Index, 10th ed. #3085 and U.S. Pat. Nos. 2,464,203 and 2,465,505; Nafoxidine, USAN and USP Dictionary of Drug Names, p. 327 (1983); CI-680, Unlisted Drugs, 28(10): 169(o) (1976); CI-628, Unlisted Drugs, 26(7): 106(1) (1974); CN-55,945-27, or nitromifene citrate, Unlisted Drugs, 27(12): 194(n) (1975); R2323 or 13-ethyl-17a-ethynl-17B-hydroxygona-4,9,11-trien-3-one, Unlisted Drugs, 23(3): 34(b) (1971); MER-25; U-11,555A; U-11,100A; ICI-46,669 and ICI-46,474; all shown in L. Terenius, et al., "Aspects on the Mode of Action of Antiestrogens and Antiprogestrogens," Hormones and Antagonists. Gynec. Invest. 3: 98; Diphenol hydrochrysene; erythro-MEA; and Park Davis CN-55,945; all disclosed in C. Geynet, et al., "Estrogens and Antiestrogens," Hormones and Antagonists. Gynec. Invest. 3: 12-13 (1972); Allenolic acid and cyclofenyl, disclosed in C. Geynet, et al., Hormones and Antagonists. Gynec. Invest. 3: 17 (1972); Chlorotrianisene, Merck Index, 10th ed., #2149; Ethamoxytriphetol, Merck Index, 10th ed., #3668; and Triparanol, Merck Index, 10th ed., #9541 and U.S. Pat. No. 2,914,562.

Various embodiments of dosage ranges are contemplated by this invention. In one embodiment, the dosage is in the range of 1-80 mg/day. In another embodiment, the dosage is in the range of 5-80 mg/day. In another embodiment the dosage is in the range of 35-66 mg/day. In another embodiment the dosage is in the range of 20-80 mg/day. In another embodiment the dosage is in the range of 20-60 mg/day. In another embodiment the dosage is in the range of 40-60 mg/day. In another embodiment the dosage is in a range of 45-60 mg/day. In another embodiment the dosage is in the range of 15-25 mg/day. In another embodiment the dosage is in the range of 55-65 mg/day. In one embodiment, the dosage is 20 mg/day. In another embodiment, the dosage is 40 mg/day. In another embodiment, the dosage is 60 mg/day. In another embodiment, the dosage is 80 mg/day.

Accordingly, the present invention provides a method of treating androgen-deprivation induced osteoporosis in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof, at a dosage of about 20 mg to about 80 mg per day of the anti-estrogen.

In another embodiment, the present invention provides a method of preventing androgen-deprivation induced osteoporosis in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof, at a dosage of about 20 mg to about 80 mg per day of the anti-estrogen.

In another embodiment, the present invention provides a method of suppressing or inhibiting androgen-deprivation induced osteoporosis in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof, at a dosage of about 20 mg to about 80 mg per day of the anti-estrogen.

In another embodiment, the present invention provides a method of reducing the risk of developing androgen-deprivation induced osteoporosis in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof, at a dosage of about 20 mg to about 80 mg per day of the anti-estrogen.

In another embodiment, the present invention provides a method of treating androgen-deprivation induced loss of BMD in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof, at a dosage of about 20 mg to about 80 mg per day of the anti-estrogen.

In another embodiment, the present invention provides a method of preventing androgen-deprivation induced loss of BMD in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof, at a dosage of about 20 mg to about 80 mg per day of the anti-estrogen.

In another embodiment, the present invention provides a method of suppressing or inhibiting androgen-deprivation induced loss of BMD in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof, at a dosage of about 20 mg to about 80 mg per day of the anti-estrogen.

In another embodiment, the present invention provides a method of reducing the risk of developing androgen-deprivation induced loss of BMD in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof, at a dosage of about 20 mg to about 80 mg per day of the anti-estrogen.

In another embodiment, the present invention provides a method of treating androgen-deprivation induced bone fractures in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof, at a dosage of about 20 mg to about 80 mg per day of the anti-estrogen.

In another embodiment, the present invention provides a method of preventing androgen-deprivation induced bone fractures in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof, at a dosage of about 20 mg to about 80 mg per day of the anti-estrogen.

In another embodiment, the present invention provides a method of suppressing or inhibiting androgen-deprivation induced bone fractures in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof, at a dosage of about 20 mg to about 80 mg per day of the anti-estrogen.

In another embodiment, the present invention provides a method of reducing the risk of developing androgen-deprivation induced bone fractures in a male subject suffering from prostate cancer, the method comprising the step of administering to said subject an anti-estrogen agent and/or its analog, derivative, isomer, metabolite, pharmaceutically acceptable salt, pharmaceutical product, hydrate, N-oxide, or any combination thereof, at a dosage of about 20 mg to about 80 mg per day of the anti-estrogen.

In one embodiment the anti-estrogen is a selective estrogen receptor modulator (SERM). In another embodiment, the anti-estrogen is a triphenylethylene. In another embodiment, the anti-estrogen is Toremifene.

In one embodiment, the anti-estrogen is administered at a daily dosage of about 20 mg. In another embodiment, the anti-estrogen is administered at a daily dosage of about 40 mg. In another embodiment, the anti-estrogen is administered at a daily dosage of about 60 mg. In another embodiment, the anti-estrogen is administered at a daily dosage of about 80 mg.

In one embodiment, the anti-estrogen is Toremifene, which is administered at a daily dosage of about 20 mg. In another embodiment, the anti-estrogen is Toremifene, which is administered at a daily dosage of about 40 mg. In another embodiment, the anti-estrogen is Toremifene, which is administered at a daily dosage of about 60 mg. In another embodiment, the anti-estrogen is Toremifene, which is administered at a daily dosage of about 80 mg.

Osteoporosis is a systemic skeletal disease, characterized by low bone mass and deterioration of bone tissue, with a consequent increase in bone fragility and susceptibility to fracture. In osteoporotic patients, bone strength is abnormal, with a resulting increase in the risk of fracture. Osteoporosis depletes both the calcium and the protein collagen normally found in the bone, resulting in either abnormal bone quality or decreased bone density. Bones that are affected by osteoporosis can fracture with only a minor fall or injury that normally would not cause a bone fracture. The fracture can be either in the form of cracking (as in a hip fracture) or collapsing (as in a compression fracture of the spine). The spine, hips, and wrists are common areas of osteoporosis bone fractures, although fractures can also occur in other skeletal areas.

BMD is a measured calculation of the true mass of bone. The absolute amount of bone as measured by bone mineral density (BMD) generally correlates with bone strength and its ability to bear weight. By measuring BMD, it is possible to predict fracture risk in the same manner that measuring blood pressure can help predict the risk of stroke.

BMD in one embodiment can be measured by known bone-mineral content mapping techniques. Bone density of the hip, spine, wrist, or calcaneus may be measured by a variety of techniques. The preferred method of BMD measurement is dual-energy x-ray densitometry (DXA). BMD of the hip, antero-posterior (AP) spine, lateral spine, and wrist can be measured using this technology. Measurement at any site predicts overall risk of fracture, but information from a specific site is the best predictor of fracture at that site. Quantitative computerized tomography (QCT) is also used to measure BMD of the spine. See for example, "Nuclear Medicine: "Quantitative Procedures" by Wahner H W, Dunn W L, Thorsen H C, et al, published by Toronto Little, Brown & Co., 1983, (see pages 107-132). An article entitled "Assessment of Bone Mineral Part 1" appeared in the Journal of Nuclear Medicine, pp 1134-1141, (1984). Another article entitled "Bone Mineral Density of The Radius" appeared in Vol. 26, No. 11, (1985) November Journal of Nuclear Medicine at pp 13-39. Abstracts on the use of gamma cameras for bone-mineral content measurements are (a) S. Hoory et al, Radiology, Vol. 157(P), p. 87 (1985), and (b) C. R. Wilson et al, Radiology, Vol. 157(P), p. 88 (1985).

The present invention provides a safe and effective method for treating, preventing, suppressing, inhibiting or reducing the risk of developing androgen-deprivation induced osteoporosis and/or loss of BMD and is particularly useful for treating male subjects suffering from prostate cancer having an elevated risk of developing androgen-deprivation induced osteoporosis. In one embodiment, the male subject is a mammalian subject. In another embodiment, the male subject is a human subject.

Furthermore, the anti-estrogens presented herein are effective at treating, suppressing or inhibiting osteopenia accompanied by bone loss. "Osteopenia" refers to decreased calcification or density of bone. This is a term that encompasses all skeletal systems in which such a condition is noted.

As contemplated herein, the present invention relates to the use of an anti-estrogen compound and/or its analog, derivative, isomer, metabolite, pharmaceutically acceptable salt, pharmaceutical product, hydrate, N-oxide, or combinations thereof for treating, preventing, suppressing, inhibiting or reducing the risk of developing androgen-deprivation induced osteoporosis and/or loss of BMD at a dosage of about 20 mg to about 80 mg per day of the anti-estrogen. Thus, in one embodiment, the methods of the present invention comprise administering an analog of the anti-estrogen. In another embodiment, the methods of the present invention comprise administering a derivative of the anti-estrogen. In another embodiment, the methods of the present invention comprise administering an isomer of the anti-estrogen. In another embodiment, the methods of the present invention comprise administering a metabolite of the anti-estrogen. In another embodiment, the methods of the present invention comprise administering a pharmaceutically acceptable salt of the anti-estrogen. In another embodiment, the methods of the present invention comprise administering a pharmaceutical product of the anti-estrogen. In another embodiment, the methods of the present invention comprise administering a hydrate of the anti-estrogen. In another embodiment, the methods of the present invention comprise administering an N-oxide of the anti-estrogen. In another embodiment, the methods of the present invention comprise administering any of a combination of an analog, derivative, isomer, metabolite, pharmaceutically acceptable salt, pharmaceutical product, hydrate or N-oxide of the anti-estrogen.

As defined herein, the term "isomer" includes, but is not limited to, optical isomers and analogs, structural isomers and analogs, conformational isomers and analogs, and the like.

In one embodiment, this invention encompasses the use of various optical isomers of the anti-estrogen compound. It will be appreciated by those skilled in the art that the anti-estrogens of the present invention contain at least one chiral center. Accordingly, the anti-estrogens used in the methods of the present invention may exist in, and be isolated in, optically active or racemic forms. Some compounds may also exhibit polymorphism. It is to be understood that the present invention encompasses any racemic, optically active, polymorphic, or stereoisomeric form, or mixtures thereof, which form possesses properties useful in the treatment of androgen-related conditions described herein. In one embodiment, the anti-estrogens are the pure (R)-isomers. In another embodiment, the anti-estrogens are the pure (S)-isomers. In another embodiment, the anti-estrogens are a mixture of the (R) and the (S) isomers. In another embodiment, the anti-estrogens are a racemic mixture comprising an equal amount of the (R) and the (S) isomers. It is well known in the art how to prepare optically active forms (for example, by resolution of the racemic form by recrystallization techniques, by synthesis from optically active starting materials, by chiral synthesis, or by chromatographic separation using a chiral stationary phase).

The invention includes "pharmaceutically acceptable salts" of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

This invention further includes derivatives of the anti-estrogens. The term "derivatives" includes but is not limited to ether derivatives, acid derivatives, amide derivatives, ester derivatives and the like. In addition, this invention further includes hydrates of the anti-estrogen compounds. The term "hydrate" includes but is not limited to hemihydrate, monohydrate, dihydrate, trihydrate and the like.

This invention further includes metabolites of the anti-estrogen compounds. The term "metabolite" means any substance produced from another substance by metabolism or a metabolic process.

This invention further includes pharmaceutical products of the anti-estrogen compounds. The term "pharmaceutical product" means a composition suitable for pharmaceutical use (pharmaceutical composition), as defined herein.

In addition, the invention encompasses pure (Z)- and (E)-isomers of the anti-estrogen compounds defined herein and mixtures thereof as well as pure (RR, SS)- and (RS, SR)-enantiomer couples and mixtures thereof.

Pharmaceutical Compositions

In one embodiment, the methods of the present invention comprise administering a pharmaceutical composition comprising the anti-estrogen and/or its analog, derivative, isomer, metabolite, pharmaceutically acceptable salt, pharmaceutical product, hydrate, N-oxide, or any combination thereof; and a pharmaceutically acceptable carrier. The pharmaceutical composition is administered to a male subject suffering from prostate cancer; for treating and/or preventing androgen-deprivation induced osteoporosis and/or loss of BMD; for suppressing or inhibiting androgen-deprivation induced osteoporosis and/or loss of BMD; and/or for reducing the risk of developing androgen-deprivation induced osteoporosis and/or loss of BMD in the male subject.

As used herein, "pharmaceutical composition" means a "therapeutically effective amount" of the active ingredient, i.e. the anti-estrogen, together with a pharmaceutically acceptable carrier or diluent. A "therapeutically effective amount" as used herein refers to that amount which provides a therapeutic effect for a given condition and administration regimen.

The pharmaceutical compositions containing the anti-estrogen can be administered to a subject by any method known to a person skilled in the art, such as parenterally, paracancerally, transmucosally, transdermally, intramuscularly, intravenously, intradermally, subcutaneously, intraperitonealy, intraventricularly, intracranially, intravaginally or intratumorally.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the anti-estrogen compounds are formulated in a capsule. In accordance with this embodiment, the compositions of the present invention comprise, in addition to the anti-estrogen active compound and the inert carrier or diluent, a hard gelating capsule.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intraarterially and are thus formulated in a form suitable for intraarterial administration. In another embodiment, the pharmaceutical compositions are administered intramuscularly and are thus formulated in a form suitable for intramuscular administration.

Further, in another embodiment, the pharmaceutical compositions are administered topically to body surfaces and are thus formulated in a form suitable for topical administration. Suitable topical formulations include gels, ointments, creams, lotions, drops and the like. For topical administration, the anti-estrogen agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of anti-estrogen agent over a period of time.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled-release compositions, i.e. compositions in which the anti-estrogen compound is released over period of time after administration. Controlled- or sustained-release compositions include formulation in lipophilic depots (e.g. fatty acids, waxes, oils). In another embodiment, the composition is an immediate-release composition, i.e. a composition in which all of the anti-estrogen compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled-release systems are discussed in the review by Langer (Science 249:1527-1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the anti-estrogen agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the anti-estrogen agents or their physiologically tolerated derivatives such as salts, esters, N-oxides, and the like are converted into a solution, suspension, or emulsion, if desired with the substances customary and suitable for this purpose, for example, solubilizers or other substances.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the anti-estrogens are pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts, which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

As defined herein, "contacting" means that the anti-estrogen compound of the present invention is introduced into a sample containing the enzyme in a test tube, flask, tissue culture, chip, array, plate, microplate, capillary, or the like, and incubated at a temperature and time sufficient to permit binding of the anti-estrogen to the enzyme. Methods for contacting the samples with the anti-estrogen or other specific binding components are known to those skilled in the art and may be selected depending on the type of assay protocol to be run. Incubation methods are also standard and are known to those skilled in the art.

In another embodiment, the term "contacting" means that the anti-estrogen compound of the present invention is introduced into a subject receiving treatment, and the anti-estrogen compound is allowed to come in contact with the androgen receptor in vivo.

As used herein, the term "treating" includes preventative as well as disorder remitative treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a subject in contact with an anti-estrogen compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, the methods of the present invention comprise administering an anti-estrogen compound as the sole active ingredient. However, also encompassed within the scope of the present invention are methods for hormone therapy, for treating prostate cancer, for delaying the progression of prostate cancer, and for preventing and/or treating the recurrence of prostate cancer, which comprise administering the anti-estrogen compounds in combination with one or more therapeutic agents. These agents include, but are not limited to: LHRH analogs, reversible antiandrogens (such as bicalutamide or flutamide), additional anti-estrogens, anticancer drugs, 5-alpha reductase inhibitors, aromatase inhibitors, progestins, selective androgen receptor modulators (SARMS) or agents acting through other nuclear hormone receptors.

Thus, in one embodiment, the methods of the present invention include using compositions and pharmaceutical compositions comprising an anti-estrogen, in combination with an LHRH analog. In another embodiment, the methods of the present invention include using compositions and pharmaceutical compositions comprising an anti-estrogen, in combination with a reversible antiandrogen. In another embodiment, the methods of the present invention include using compositions and pharmaceutical compositions comprising an anti-estrogen, in combination with an additional anti-estrogen. In another embodiment, the methods of the present invention include using compositions and pharmaceutical compositions comprising an anti-estrogen, in combination with an anticancer drug. In another embodiment, the methods of the present invention include using compositions and pharmaceutical compositions comprising an anti-estrogen, in combination with a 5-alpha reductase inhibitor. In another embodiment, the methods of the present invention include using compositions and pharmaceutical compositions comprising an anti-estrogen, in combination with an aromatase inhibitor. In another embodiment, the methods of the present invention include using compositions and pharmaceutical compositions comprising an anti-estrogen, in combination with a progestin. In another embodiment, the methods of the present invention include using compositions and pharmaceutical compositions comprising an anti-estrogen, in combination with a SARM. In another embodiment, the methods of the present invention include using compositions and pharmaceutical compositions comprising an anti-estrogen, in combination with an agent acting through other nuclear hormone receptors.

The following examples are presented in order to more fully illustrate the preferred embodiments of the invention. They should in no way, however, be construed as limiting the broad scope of the invention.

EXPERIMENTAL DETAILS SECTION

EXAMPLE 1

Effect of Toremifene on Bone Turnover in Human Male Subjects

In a Phase IIa clinical trial to determine whether Toremifene has chemopreventive activity against prostate cancer, 18 men with high-grade prostatic intraepithelial neoplasia (HGPIN) were treated with 60 mg/d of Toremifene for 4 months. At Day 120 there was a significant reduction from baseline in serum calcium (mean $-0.12$, $p=0.005$) and at both day 60 and day 120, alkaline phosphatase was significantly decreased compared to baseline (mean=$-18.7$ at Day 60 and $-21.0$ at Day 120, and $p<0.001$ for both visits).

These clinical data demonstrate that the anti-estrogen Toremifene showed estrogenic effects on bone favorably affecting bone turnover markers in men.

EXAMPLE 2

Effect of Toremifene on Bone in Male Rats

Drug Delivery System

The test article, positive control and placebo were delivered by ALZA pumps manufactured by Durect Corporation (Cupertino, Calif.). Pumps were implanted in a subcutaneous pocket using appropriate surgical technique. The pumps employed in this study deliver a continuous rate of drug over a 30-day period with Toremifene formulated to release 1.8 mg/day (2 mL pump) and 17-β-Estradiol (positive control) released at 70 ug/day. Data provided by the manufacturer of the pumps validates the constant rate of drug delivery over a 28-day period, and suggests that the constant rate can be expected for several additional days. Animals were anesthetized and pump replacement was performed for each dosage group on days 31, 61, and 91 to provide drug administration over a 120-day period. Every animal on study had a pellet implanted to control for potential confounding variables associated with surgery for implantation.

Study Groups:

Adult male Sprague-Dawley rats (14-weeks old at start of study), weighing approximately 0.35 kg, were used in the experiments. This study employed five test groups of 12 rats. Treatment groups represent placebo control (castrated and sham operated), 17-β-estradiol (castrated) and Toremifene (castrated and sham operated). 5 animals from each treatment group were sacrificed at day 60 and day 120, and bone metabolism markers were measured and bone was harvested for biomechanical strength and density testing.

TABLE 1

Treatment groups for Effects of Toremifene on Bone

| Group | Drug | Sham | Castrated | # of animals | Sacrifice Schedule (days) |
|---|---|---|---|---|---|
| 1 | Placebo control | ✓ | | 5 | 60 |
| 2 | Placebo control | ✓ | | 5 | 120 |
| 3 | Toremifene (1.75 mg/day) | ✓ | | 5 | 60 |
| 4 | Toremifene (1.75 mg/day) | ✓ | | 5 | 120 |
| 5 | Estradiol (0.07 mg/day) | | ✓ | 5 | 60 |
| 6 | Estradiol (0.07 mg/day) | | ✓ | 5 | 120 |
| 7 | Placebo control | | ✓ | 5 | 60 |
| 8 | Placebo control | | ✓ | 5 | 120 |
| 9 | Toremifene (1.75 mg/day) | | ✓ | 5 | 60 |
| 10 | Toremifene (1.75 mg/day) | | ✓ | 5 | 120 |

Observations:

Clinical Observations: Cage-side observations were made and recorded once weekly (daily cage checks note any exceptions). Effects on vital functions were observed. Any animals found moribund or presenting with signs of acute toxicity were anesthetized by an intramuscular ketamine/xylazine (87/13) injection and euthanized by abdominal aorta exsanguinations.

Body Weight: Body weights were taken in triplicate and averaged once per week.

Sacrifices were made at 60 and 120 days. Each sacrifice involved 5 rats from each treatment group, and 2 rats at 30, 60, 90, and 120 days to verify drug in plasma (refer to Table 1 for group allocation to treatment and sacrifice). Animals were anesthetized by an injection of ketamine/xylazine (87/13) and sacrificed by abdominal aorta exsanguinations. Blood collected at exsanguinations was processed to collect serum.

Bone remodeling was assessed per serum markers to analyze bone resorption and bone formation of treatment rats. The tests listed in Table 2 indicate the bone remodeling category and the amounts of serum required for analysis. Serum chemistry analysis of blood calcium, phosphorus, bilirubin and creatinine levels, and bone-specific alkaline phosphatase, were performed at AniLytics, Inc. (Gaithersburg, Md.).

TABLE 2

Assays for serum markers of bone remodeling in mouse

| Remodeling Category | Tests Run | Test Supplier | Minimum Serum Required |
|---|---|---|---|
| Bone Formation | Rat-MID Osteocalcin ELISA | OSTEOMETER | 20 ul |
| | Chemistry Analysis of Calcium, Phosphorus, Billirubin, Creatine | AniLytics, Inc. | 70 ul |
| | Bone Spec. Phosphatase | AniLytics, Inc. | 50 ul |
| Bone Resorption | Serum CrossLaps One Step ELISA | OSTEOMETER | 20 ul |
| | (Deoxy)Pyridinoline Crosslink in serum | METRA | 25 ul |
| | RatTRAP ELISA (tartrate-resistant Acid P) | SBA Sciences | 50 ul |

Processed for Serum. Serum was aliquoted and frozen at −80° C. until analysis. Serum tests were performed at GTx, Inc. for osteocalcin levels (bone formation marker) and c-telopeptide (bone resorption marker). After the femur was removed from each animal, it was stripped of extraneous tissue, and stored at −20° C. until biomechanical strength and bone mineral density analysis.

Randomization/Assignment to Groups:

Prior to study, 10 groups were randomized to treatments, then sixty (60) 12 week-old rats were ordered, ear-tagged and weighed by the Manager of Animal Resources. Sixty animals were then randomized to the 10 treatment groups of 6 animals each. An ANOVA was performed to establish the presence or absence of significant difference in body weight (within 10% of average body weight is acceptable). The population was already restricted and could not be restricted further. If there was a significant difference, it was duly noted, but changes in assignment were not made. Bone parameters were not normalized to body weight. Values for bone parameters are reported as absolute and evaluated based on group means compared to the appropriate controls.

Compounds

Test Article 1:

Identification: Toremifene

Description: White crystalline powder that is extracted from Toremifene tablets as active ingredient.

Test Article 2 (Positive Control):

Identification: 17-β-Estradiol (Sigma Aldrich, for laboratory research use).

EXAMPLE 3

Effect of Toremifene on Bone Density and Serum Markers for Bone Remodeling in Male Rats The purpose of this study is to determine whether administration of Toremifene to mature male rats is bone sparing as can presently be measured by the levels of bone-specific serum markers that indicate bone resorption and formation (where 17-β-Estradiol is used as a positive control). The effect of Toremifene (and 17-β-Estradiol) on androgen deprivation-induced bone loss was also determined through bone density and mechanical strength testing.

The model used herein is an orchidectomy model, which is an experimental model used to mimic the type of androgen deprivation that would be caused by, for example, LHRH agonist therapy in prostate cancer.

Materials and Methods

Study Design

Male Sprague-Dawley rats (Harlan Sprague Dawley) were placed on study at 14-weeks of age. They were randomized and divided into five treatment groups: vehicle only (placebo, or P) after sham operation, vehicle only after orchidectomy (Orx), Toremifene (5 mg/kg/day) after sham-operation, and Toremifene after orchidectomy, and 17-β-estradiol (0.5 mg/kg/day) after orchidectomy. Test articles were delivered subcutaneously by Alzet pumps. Pumps were re-implanted every 30 days until the end of the study. Five to six animals from each group were sacrificed after 60 and 120 days of treatment, and femurs were harvested, stripped of soft tissue and muscle, and stored individually in polypropylene vials at −80° C. until analysis of bone density and mechanical strength testing. Additionally, serum was collected on days 15, 30, 60, 90 and 120, to measure markers of bone metabolism and to perform serum chemistry.

After collection, serum was divided into 3 aliquots and stored at −80° C. until analysis. 125 ul for serum biochemistry performed by AniLytics, Gaithersburg, Md. (Bone-Specific Alkaline Phosphatase, Calcium, Phosphorus, Creatinine and Bilirubin). 100 ul for serum Rat Osteocalcin ELISA and Serum RatLaps ELISA for C-terminal telopeptides determination. The rest of the collected serum was left for repeated test if necessary.

Bones were stripped of soft tissue and muscles and stored individually in 15 ml vials at −80 C, until further testing.

Analysis of Bone Turnover Markers from Rat Serum

Serum RatLaps ELISA, Osteometer BioTech A/S, Denmark

The assay was performed in duplicates, each 20 ul of serum as well as standards and control. Briefly, 100 ul of Biotinylated RatLaps Antigen was incubated 30 min in each well, strips were washed and 20 ul of Standard, Control and unknown samples were added to appropriate wells, followed by 100 ul of primary antibody (polyclonal Ab raised against a synthetic peptide EKSQDGGR specific for a part of the C-terminal telopeptide alpha 1 chain of rat type I collagen). After overnight incubation at 4 C., the wells were washed and 100 ul of Peroxidase conjugated Goat anti-Rabbit IgG Antibody was added to each well and incubated 60 min. After washing the strips 100 ul of the Chromogenic Substrate Solution was added to each well, and after 15 min the reaction was stopped and the absorbance was measured at 450 nm. The means of the duplicate absorbance determination were calculated, and a standard curve was constructed using 4-parametric logistic curve fit. Sample RatLaps concentrations were determined by interpolation.

Rat Osteocalcin EIA, Biomedical Technologies, MA

This assay is specific for rat Osteocalcin and both carboxylated and decarboxylated rat Osteocalcin are recognized. A monoclonal antibody against the N-terminal region of Osteocalcin is bound to the polystyrene wells. The assay was performed in duplicates. 100 ul of standards, control and 1 to 20 diluted samples were added to appropriate wells and incubated overnight at 4 C. After washing the strips, 100 ul of Goat polyclonal antibody of high specificity for C-terminus of rat Osteocalcin was added and incubated 60 min at 37 C. After washing, 100 ul of Donkey anti-goat IgG peroxidase conjugated antibody was added and incubated 60 min at 22 C. The wells were washed and a mix of TMB and peroxide solution was added and incubated 30 min at 22 C in the dark. The reaction was stopped, and the absorbance was measured at 450 nm. A standard curve was constructed using 4-parametric logistic curve fit. Sample osteocalcin concentrations were determined by interpolation.

Bone Analysis Methodology

Peripheral Quantitative Computed Tomography (pQCT)

Right femurs were subjected to pQCT analysis using a Stratec XCT-RM with associated software (Stratec Medizintechnik GmbH, Pforzheim, Germany. Software version 5.40 C). Femurs were scanned at two sites, 20% and 50% of the total femoral length measured from the distal femur. The position was verified using scout views, and scan results from two 0.5 mm slices perpendicular to the long axis of the femur shaft were recorded.

Mechanical Testing

Using a Material Testing System (Model 5501R Instron Corp., Canton, Mass.), two types of mechanical testing were performed on the right femur. The load and extension curves were collected by the machine software (Merlin II, Instron Corp.). All tests were conducted using a 5 kN load cell at a constant loading rate of 6 mm/min. The general applications of the tests were as described in Turner and Burr (*Bone*, 1993; 14: 595-608) and Ke et al (*Bone*, 1998; 23, 249-255).

Compression Test of the Distal Femur

A compression test was used to determine the mechanical properties of the distal femur. The distal femur test specimen was obtained by removing a 3 mm segment directly proximal to the distal condyle using a slow speed diamond saw with constant saline irrigation. An electronic caliper was used to measure the average anterior/posterior diameter (a), medial/lateral diameter (b), and height (h) of the bone. The extrinsic parameters, maximal load ($F_u$), stiffness (S) and energy (W), were obtained from the load and extension curve. The following intrinsic parameters were calculated from the measured values: Cross sectional area $(CSA)=(\pi*a*b)/4$; Ultimate Strength $(\sigma)=F_u/CSA$; Elastic modulus $(E)=S/(CSA/h)$; Toughness $(T)=W/(CSA*h)$.

Results/Discussion

Analysis of Serum Markers of Bone Turnover

Bone turnover markers have been demonstrated as an effective, validated tool for the clinical scientist to monitor bone activity. Ultimately, the data of greatest consequence to evaluate novel therapeutics aimed at osteoporosis treatment and prevention is a demonstrated improvement in the quality of bone itself. However, because changes in bone turnover markers correlate well with bone strength testing, in the present study C-telopeptide and osteocalcin levels were analyzed for interim analysis and supplementary data to support of the effectiveness of treatment.

C-telopeptide of Type I Collagen:

As demonstrated in FIG. 1, C-telopeptide levels in orchidectomized animals were slightly increased by 22 and 9.5% over the placebo 15 and 30 day groups, respectively, indicating that, after castration, bone resorptive activity is increased and type I collagen is being degraded, with fragments containing the cross-linked molecules released into the blood. Further, treatment of orchidectomized animals with toremifene and the positive control, 17-β-estradiol, reduced the C-telopeptide levels to or below control values (i.e. unorchidectomized, placebo-treated animals), with the 30 day treatment trending to significance for the 17-β-estradiol group.

Because toremifene and 17-β-estradiol decrease the level of C-telopeptide in the serum, the data indicate that these agents are acting to prevent the resorption of bone induced by androgen deprivation.

Figure 2:
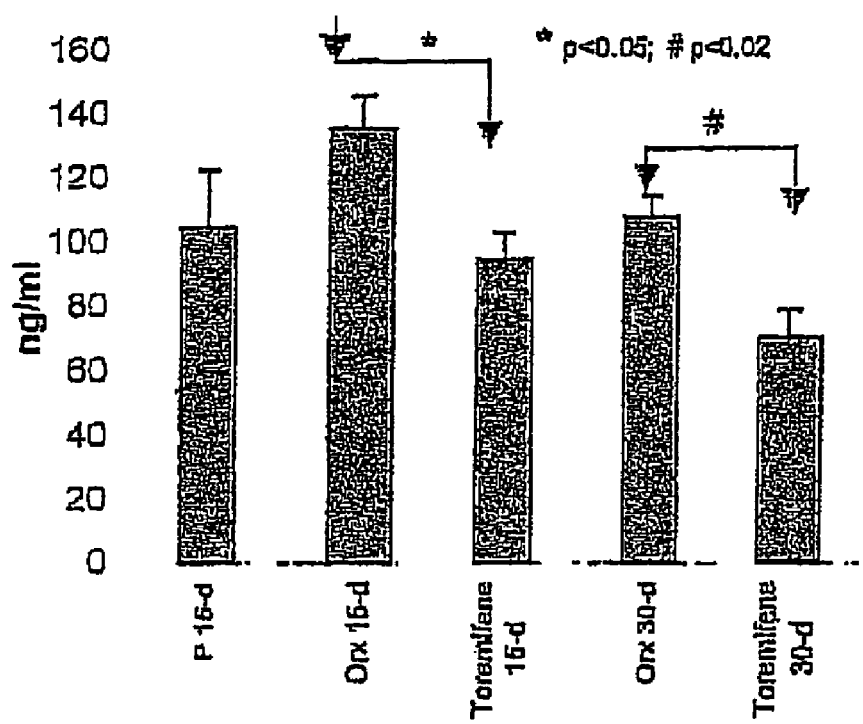
FIG. 2: Effect of Toremifene on serum osteocalcin levels. A) 10 and 30 days; B) 60 and 120 days.

Osteocalcin:

Applicants demonstrated that osteocalcin levels were increased by castration. Toremifene significantly reduced the osteocalcin levels in castrated animals to intact control levels (p<0.05 at 15 days, and p<0.02 at 30 days, FIG. 2A). The increases in osteocalcin levels were most pronounced 15 days after castration, although Toremifene and 17-β-estradiol continued to significantly reduce osteocalcin levels to below that of intact control rats for up to 120 days (FIG. 2B). These results indicate that the rate of bone formation in males is upregulated following orchidectomy to compensate for increased resorptive activity. 17-β-Estradiol, and the selective estrogen receptor modulator toremifene, stabilize the bone resorption and formation processes, hence decreasing overall osteocalcin levels that are detectable in serum.

Biomechanical Analysis of Bone

Androgen deficiency, induced by castration, has been used as a model of male osteoporosis. In this model, most of the bone loss occurs in cancellous bone. To further understand the effects of toremifene on bone mineral density and mechanical strength, bones were harvested upon completion of the in-life study phase and sent to SkeleTech (Bothell, Wash.) for testing. All bones were thawed in physiological saline prior to analysis. Statistical analysis was performed using SAS software (SAS Institute, Cary, N.C.). One-way analysis of variance (group) was performed. Individual group differences were ascertained with Dunnett's procedure using treatment group 2 (Castrated+Placebo) as the reference group. A p value of <0.05 was considered significant. Where appropriate, a p value of <0.1 is noted as a trend (when the treatment results are in the direction of the positive control).

Distal Right Femur Cancellous pQCT:

Total bone mineral content and density were lower, though not statistically significant, in Orx animals when compared to Sham-operated animals. Both Toremifene and 17-β-Estradiol treatment appeared to reduce total bone area and increase total bone mineral density. Cancellous bone mineral content and density in Orx animals were 34% less than in Sham-operated animals. Toremifene partially prevented this decrease whereas 17-β-Estradiol was able to fully prevent this cancellous bone loss. None of the parameters produced statistically significant differences from the Orx group due to the small sample size and the large variations in the measured results. The results are summarized in Table 3.

TABLE 3

Summary of the Distal Right Femur Cancellous pQCT

| Treatment Group | | Total Bone Content (mg/mm) | Total Bone Area (mm$^2$) | Total Bone Density (mg/cm$^3$) | Trabecular Content (mg/mm) | Trabecular Area (mm$^2$) | Trabecular Density (mg/cm$^3$) |
|---|---|---|---|---|---|---|---|
| Sham | | 11.47 | 17.41 | 658.27 | 1.65 | 7.83 | 209.72 |
| (n = 6) | S.E.M. | 0.89 | 0.97 | 32.81 | 0.43 | 0.44 | 52.17 |
| | p < 0.05 | n.s. | n.s. | n.s. | n.s. | n.s. | n.s. |
| Cx | Mean | 11.07 | 17.38 | 639.50 | 1.08 | 7.82 | 138.38 |
| (n = 5) | S.E.M. | 0.50 | 1.26 | 47.07 | 0.22 | 0.57 | 31.88 |
| | p < 0.05 | n.a. | n.a. | n.a. | n.a. | n.a. | n.a. |
| Cx + Toremifene | Mean | 10.69 | 15.96 | 669.74 | 1.13 | 7.18 | 157.56 |
| (n = 5) | S.E.M. | 0.48 | 0.67 | 21.95 | 0.22 | 0.30 | 32.77 |
| | p < 0.05 | n.s. | n.s. | n.s. | n.s. | n.s. | n.s. |
| Cx + EST | Mean | 11.01 | 15.95 | 690.74 | 1.52 | 7.17 | 210.28 |
| (n = 5) | S.E.M. | 0.76 | 0.98 | 26.68 | 0.50 | 0.44 | 62.69 |
| | p < 0.05 | n.s. | n.s. | n.s. | n.s. | n.s. | n.s. | p < 0.05 vs. TG2.
n.s. = not significant
n.a. = not applicable

Compression Test of the Distal Femur:

Mechanical strength was tested at the distal femur, a site rich in cancellous bone. Maximum load, stiffness, ultimate strength, and elastic modulus were lower in Orx animals when compared to Sham-operated animals. Toremifene treatment of Orx animals improved various parameters to a level that was better than Sham-operated animals. 17-β-Estradiol treatment showed statistically significant improvements in these parameter values. Cross-sectional area was decreased in toremifene and 17-β-Estradiol treated Orx animals as expected from pQCT data The results are summarized in Table 4.

TABLE 4

Summary of the Distal Right Femur Compression Test

| Treatment Group | | Maximum Load (N) | Stiffness (N/mm) | Energy (mJ) | Ultimate Strength (N/mm$^2$) | Elastic Modulus (MPa) | Toughness (MJ/mm$^3$) | CSA (mm$^2$) | Height (mm) |
|---|---|---|---|---|---|---|---|---|---|
| Sham | | 420.04 | 3400.22 | 43.10 | 18.95 | 481.38 | 0.62 | 22.32 | 3.13 |
| (n = 6) | S.D. | 123.75 | 944.50 | 13.09 | 5.86 | 152.38 | 0.18 | 1.64 | 0.14 |
| | p < 0.05 | n.s. | n.s. | n.s. | n.s. | n.s. | n.s. | n.s. | n.s. |
| Cx | | 386.80 | 2538.96 | 49.97 | 16.73 | 341.02 | 0.68 | 23.19 | 3.14 |
| (n = 5) | S.D. | 70.43 | 887.56 | 18.45 | 3.33 | 109.52 | 0.23 | 1.28 | 0.10 |
| | p < 0.05 | n.a. | n.a. | n.a. | n.a. | n.a. | n.a. | n.a. | n.a. |
| Cx + Toremifene | | 467.01 | 3856.71 | 56.96 | 22.13 | 579.07 | 0.86 | 21.30 | 3.15 |
| (n = 5) | S.D. | 125.89 | 1303.56 | 17.07 | 6.34 | 211.70 | 0.30 | 1.43 | 0.15 |
| | p < 0.05 | n.s. | n.s. | n.s. | n.s. | n.s. | n.s. | n.s. | n.s. |
| Cx + EST | | 613.61 | 4842.67 | 58.28 | 31.23 | 753.44 | 0.98 | 19.75 | 3.06 |
| (n = 5) | S.D. | 72.10 | 740.18 | 18.39 | 4.76 | 136.97 | 0.34 | 1.14 | 0.12 |
| | p < 0.05 | * | * | n.s. | * | * | n.s. | * | n.s. | p < 0.05 vs. TG2.
n.s. = not significant
n.a. = not applicable

SUMMARY

Androgen deficiency model resulted in animals that had increased levels of the bone resorption marker C-telopeptide as well as osteocalcin in serum. Treatment with toremifene and 17-β-estradiol significantly reduced the levels of these serum markers following castration. Further, androgen deficiency resulted in a 34% loss of cancellous bone mineral content and density. Importantly, the use of toremifene partially prevented this loss. As predicted, estrogen was very effective in preventing cancellous bone loss due to androgen deficiency. Additionally, the compression test of the distal femur showed improved strength parameters in orchidectomized groups treated with toremifene, and statistically significant improvements with estrogen treatment. These measurements are partially correlated with total bone mineral density at that site. In conclusion, the data presented herein demonstrates that the selective estrogen receptor modulator toremifene has a positive effect for bone improvement in men undergoing androgen-deprivation therapy for prostate cancer.

EXAMPLE 4

Effect of Toremifene on Osteopenia in Male Rats

Introduction and Study Aims

The purpose of these studies is: 1) To determine the efficacy of two doses of Toremifene (Tor) in the prevention of bone loss in orchidectomized rats (ORX) as determined by bone mineral density analyses with dual energy X-ray absorptiometry (DXA) and ash mineral density; 2) To determine the efficacy of two doses of Toremifene on the mechanical strength of bone compared to vehicle-treated ORX and sham-operated rats; and to evaluate the effects of two doses of Toremifene on histomorphometric indices of bone turnover and bone structure in ORX rats.

Experimental Design

Eight month-old male Sprague Dawley rats were either sham-operated (SHAM) or orchidectomized (ORX). Treatment began immediately following surgery. The treatment groups were as described in Table 5.

TABLE 5

Treatment Groups

| | Description | Sacrifice |
|---|---|---|
| 1 | Sham + vehicle | 10 animals at wk 6 |
| 2 | Sham + vehicle | 10 animals at wk 12 |
| 3 | ORX + vehicle | 10 animals at wk 6 |
| 4 | ORX + vehicle | 10 animals at wk 12 |
| 5 | ORX + 5 mg/kg/d Toremifene | 10 animals at wk 6 |
| 6 | ORX + 5 mg/kg/d Toremifene | 10 animals at wk 12 |
| 7 | ORX + 10 mg/kg/d Toremifene | 10 animals at wk 6 |
| 8 | ORX + 10 mg/kg/d Toremifene | 10 animals at wk 12 |
| 9 | ORX + 0.2 mg/kg/d 17β-estradiol | 10 animals at wk 6 |
| 10 | ORX + 0.2 mg/kg/d 17β-estradiol | 10 animals at wk 12 |

Animals were given calcein (intraperitoneally) 12 and 2 days prior to sacrifice. Femurs and lumbar vertebra (L5) were preserved frozen wrapped in saline-soaked gauze. Tibiae and lumbar vertebrae (L4) were preserved in 10% formalin for 48 hours, then transferred to 70% ethanol for long-term storage.

Bone Analysis Techniques

Bone sites were subjected to different analysis techniques at each time point harvested, as shown in Table 6.

TABLE 6

Analysis Techniques

| Technique/Bone Site | Week 6 Specimens | Week 12 Specimens |
|---|---|---|
| DXA of the right femur | Yes | Yes |
| DXA of the lumbar vertebra (L5–L6) | No | Yes |
| Histology and histomorphometry of the right proximal tibia | Yes | Yes |
| Histology and histomorphometry of the lumbar vertebra (L4) | No | Yes |
| Ash density and Ca and Pi content in ash of the right femur | No | Yes |
| Biomechanical testing of the distal segment of the left femur | Yes | Yes |
| Biomechanical testing of the femoral shaft of the left femur | No | Yes |
| Biomechanical testing of the lumbar vertebral body (L5) | No | Yes |
| Biomechanical testing of the femoral neck of the left femur | No | Yes |

Ex Vivo Dual Energy X-Ray Absorptiometry (DXA)

Ex vivo DXA analysis was performed on the vertebra (L5) using a PIXImus instrument and associated animal research software (Lunar Corporation, Madison, Wis.). Bone mineral content (BMC), bone area (BA) and bone mineral density (BMD) are reported. Ex vivo DXA analysis was performed on the femur using a pDXA Sabre and associated animal research software (Norland Medical Systems, Inc., Fort Atkinson, Wis.). BMC, BA and BMD are reported for four regions of interest: whole femur, 25% distal femur, 25% proximal femur and 50% of midshaft femur.

Histology and Static and Dynamic Bone Histomorphometry: Approximately 1.1 cm of the proximal tibia was cut away and the frontal face was trimmed with a low-speed diamond wheel saw to expose the marrow cavity. The L4 lumbar vertebral body was prepared from the lumbar vertebra by trimming off the processes with a slow-speed diamond saw. Each proximal tibia and lumbar vertebral body was dehydrated in a series of ascending ethanol (EtOH) concentrations. Following dehydration, the bone samples were infiltrated and then embedded in a methyl methacrylate-dibutyl phthalate plastic composite. Embedded samples of the proximal tibiae were sectioned using a Leitz motorized rotary microtome equipped with a tungsten-carbide microtome knife. Once the blocks had been trimmed and faced to the sampling site, a 4-micron section was stained with Goldner's trichrome stain for bright field microscopy and an 8-micron section was left unstained for epifluorescent microscopy. Embedded lumbar vertebral body samples were also sectioned using a Leitz motorized rotary microtome equipped with a tungsten-carbide microtome knife. Once the blocks had been trimmed and faced to the sampling site, a 4-micron section was stained with Goldner's trichrome stain for bright field microscopy and an 8-micron section was left unstained for epifluorescent microscopy.

The cancellous bone in the secondary spongiosa of the proximal tibia was evaluated in a region of interest (ROI) that was 1.0 mm distal to the lowest point of the growth plate in a rectilinear region of 3×2 fields. The cancellous bone in the marrow cavity of the lumbar vertebral body was evaluated in a ROI that was approximately 0.5 mm away from the end plates and dorsal and ventral cortices.

The bone histomorphometry was performed using an OsteoMeasure software program (OsteoMetrics, Inc., Atlanta, Ga.) interfaced with a Nikon Eclipse E400 light/epifluorescent microscope and video subsystem. All slides were analyzed in a blinded manner. Total tissue area, trabecular bone area, trabecular bone perimeter and osteoclast perimeter and number were measured on 4 μm Goldner's trichrome-stained sections. Percent trabecular bone area, trabecular number, trabecular thickness, trabecular separation, osteoclast perimeter as a percentage of bone surface and osteoclast number per unit of bone surface were then calculated according to standardized formulae. For deriving the dynamic parameters, single-labeled calcein perimeter, double-labeled calcein perimeter and interlabel width (label thickness) were measured on 8 μm unstained sections. Mineralizing surface, mineral apposition rate and bone formation rate-surface, bone and tissue referents were calculated.

Ash Density and Ca and Pi Contents in Ash

Femur was cleaned of flesh and its volume determined using Archimedes' principle. Wet weight of the femur in air and in water were separately collected and volume calculated. Dry weight was obtained after the femur was dried in the drying oven. The femur was then ashed in a muffle furnace at 600° C. for at least 10 hours and the mineral content of the ashed femur was weighed. The ashed femur was then subjected to calcium and phosphorus content determinations using a routine chemistry instrument.

Measurement of Bone Mechanical Properties

Bone strength was evaluated using a compression test at the vertebral body, a three point bending test at the femoral shaft, a compression test at the distal femur and a cantilever compression test of the femoral neck. Prior to mechanical testing, all samples were thawed in cold saline and carefully cleaned of any remaining adherent soft tissue.

Results

Figure 3:
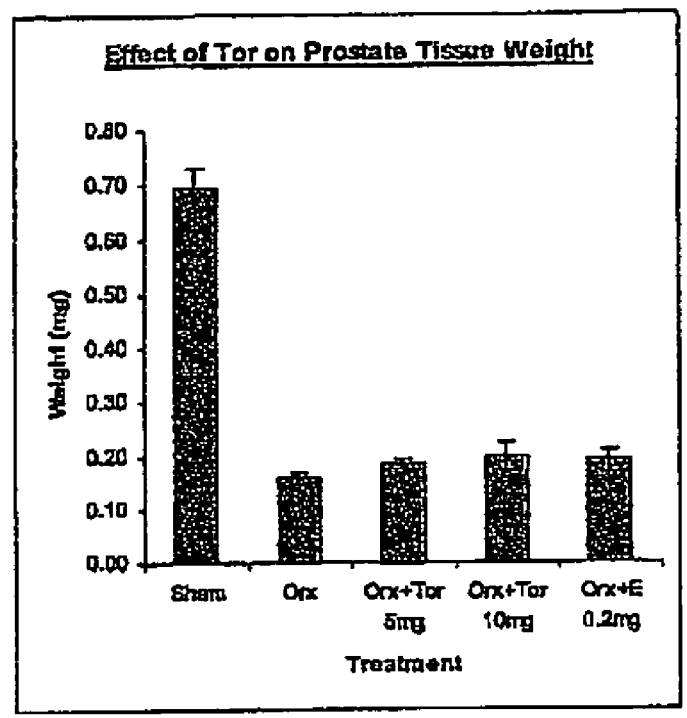
FIG. 3: Effect of Toremifene on prostate weight in the Orx rat.

Prostate Weight: Orx decreased prostate weight by 77% but E (Estradiol) or Tor had no effect on prostate weight in the Orx rat (FIG. 3).

Figure 4A:
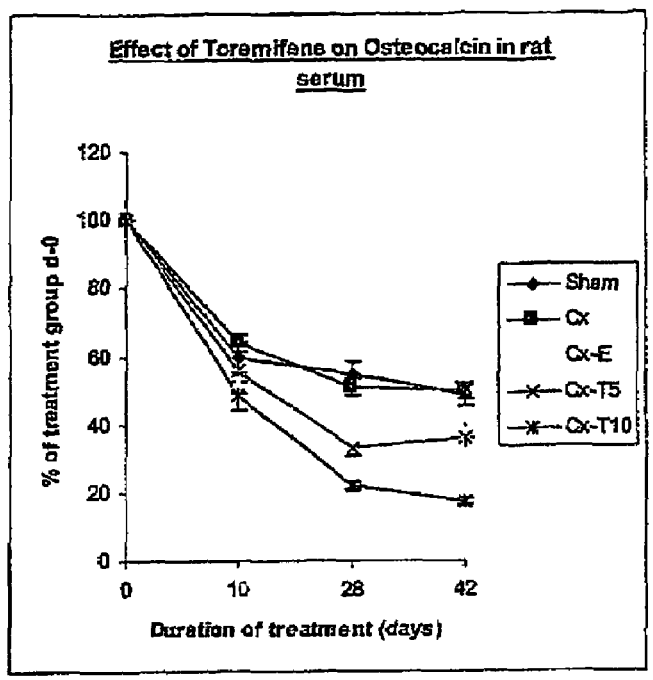
FIG. 4a: Effect of Toremifene on Osteocalin in rat serum.
Figure 4B:
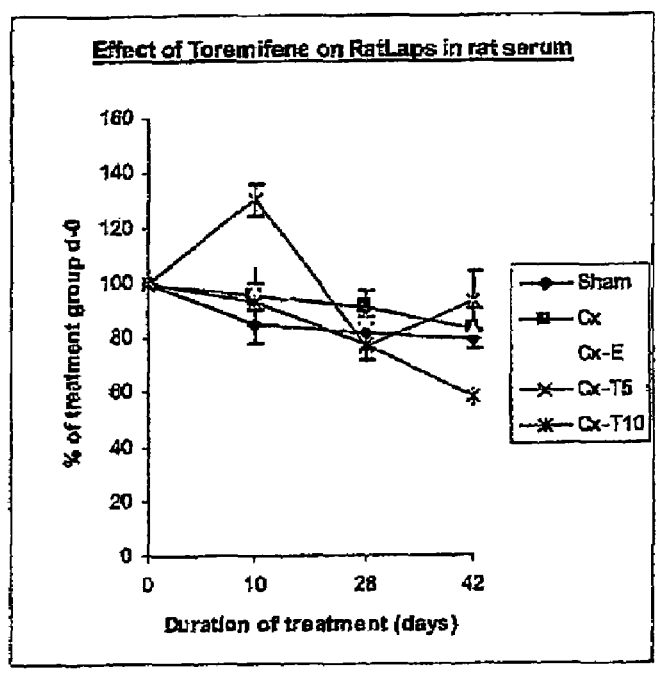
FIG. 4b: Effect of Toremifene on RatLaps in rat serum.

Bone Biochemical Markers: OC levels in Orx rats were slighlty higher than the sham group at 10 days and treatment with E, 5 mg-Tor and 10 mg-Tor all reversed OC levels to slightly below that of Sham group. Further effect of Tor was dose- and time-dependent (FIGS. 4a and 4b). Thus, the inhibitory effect of 5 mg-Tor on OC levels at 28 days was same as E and did not change further whereas that of 10 mg-Tor was more pronounced than both 5 mg Tor and E, and continued at 42 days.

CTX levels at all time points were slightly higher in Orx rats compared to the sham-operated rats. Neither E nor Tor had any effect on CTX at 10 days. However, continued treatment with E and 10 mg Tor reduced the CTX levels at 28 days, Tor being slightly more effective than E. While CTX levels did not change further with E, 10 mg-Tor treated rats had significantly lower CTX levels at 42 days when the CTX levels declined to levels lower than sham or E-treated group. Thus, the anti-resorptive activity of 10 mg-Tor continued with time and was significantly higher than E at 42 days. The effect of 5 mg Tor on CTX was not uniform and cannot be interpreted.

Static and Dynamic Bone Histomorphometry of Proximal Tibia: Orx induced a significantly elevated bone turnover state, as seen by increased osteoclast number, mineral apposition rate (MAR) and bone formation rate (BFR/BS, BFR/BV, BFR/TV) resulting in reduced trabecular bone volume at the proximal tibia This reduction in trabecular bone volume was due to a reduction in trabecular bone thickness and number, although none of these changes reached statistically significant levels. Treatment with 10 mg/kg/d Tor and E was very effective in preventing loss of trabecular bone volume.

The Orx-induced increase in bone turnover parameters was significantly inhibited by Tor and E treatment (p<0.05 vs. Orx+vehicle). Tor 5 and 10 mg/kg/d significantly reduced the Orx-induced elevation in bone turnover parameters, with results similar to treatment with 0.2 mg/kg/d E. Osteoclast number and surface were reduced to the levels of sham-operated animals while bone formation rate parameters were reduced to levels below those of sham-operated animals by either Tor or E. The reduction in bone formation rate was the result of reduced bone forming surface (mineralizing surface) and bone forming activity (MAR) after Tor or E treatment. Thus, estradiol and toremifene treatment resulted in improved bone microarchitecture. Summarized data is shown in Tables 7a and 7b.

TABLE 7a

Static and Cellular Parameters at the Proximal Tibia at 6 Wks

| Treatment Group | | Trabecular Bone Volume % | Trabecular Thickness um | Trabecular Number #/mm | Trabecular Separation um | Osteoclast Surface % | Osteoclast Number/ Bone Surface #/mm |
|---|---|---|---|---|---|---|---|
| Sham | mean | 8.77 | 50.14 | 1.70 | 582 | 5.43 | 3.11 |
| vehicle | SD | 3.62 | 6.69 | 0.49 | 183 | 1.14 | 0.58 |
| | n | 8 | 8 | 8 | 8 | 8 | 8 |
| | stat | n.s. | n.s. | n.s. | n.s. | n.s. | ** |
| Orx | mean | 6.08 | 41.91 | 1.42 | 689.67 | 9.47 | 4.92 |
| vehicle | SD | 2.17 | 7.56 | 0.29 | 152.24 | 2.19 | 1.21 |
| | n | 9 | 9 | 9 | 9 | 9 | 9 |
| | stat | n.a. | n.a. | n.a. | n.a. | n.a. | n.a. |
| Orx | mean | 5.33 | 41.39 | 1.30 | 837.67 | 6.61 | 3.98 |
| 5 mg/kg/d | SD | 1.86 | 7.94 | 0.40 | 433.65 | 1.97 | 1.39 |
| Toremifene | n | 9 | 9 | 9 | 9 | 9 | 9 |
| | stat | n.s. | n.s. | n.s. | n.s. | n.s. | n.s. |
| Orx | mean | 8.81 | 45.54 | 1.85 | 570.89 | 5.27 | 3.33 |
| 10 mg/kg/d | SD | 4.33 | 8.81 | 0.66 | 256.87 | 1.40 | 0.82 |
| Toremifene | n | 9 | 9 | 9 | 9 | 9 | 9 |
| | stat | n.s. | n.s. | n.s. | n.s. | n.s. | ** |
| Orx | mean | 8.26 | 47.11 | 1.75 | 572 | 6.35 | 3.77 |
| 0.2 mg/kg/d | SD | 2.34 | 4.37 | 0.46 | 226 | 2.33 | 1.30 |
| Estradiol | n | 8 | 8 | 8 | 8 | 8 | 8 |
| | stat | n.s. | n.s. | n.s. | n.s. | n.s. | n.s. |

TABLE 7b

Dynamic Parameters at the Proximal Tibia at 6 Wks

| Treatment Group | | Mineralizing Surface % | Mineral Apposition Rate um/day | Bone Form. Rate, Bone Surface Ref um$^3$/um$^2$/yr | Bone Form Rate, Bone Volume Ref %/yr | Bone Formation Rate, Tissue Volume Ref %/yr |
|---|---|---|---|---|---|---|
| Sham | mean | 9.02 | 0.81 | 30.00 | 126.01 | 9.55 |
| vehicle | SD | 3.27 | 0.41 | 19.80 | 93.63 | 5.33 |
| | n | 8 | 8 | 8 | 8 | 8 |
| | stat | ** | n.s. | ** | ** | ** |
| Orx | mean | 16.22 | 1.11 | 65.56 | 311.41 | 19.83 |
| vehicle | SD | 4.44 | 0.67 | 42.32 | 195.79 | 15.18 |
| | n | 9 | 9 | 9 | 9 | 9 |
| | stat | n.a. | n.a. | n.a. | n.a. | n.a. |
| Orx | mean | 6.67 | 0.32 | 10.78 | 58.20 | 2.30 |
| 5 mg/kg/d | SD | 4.82 | 0.31 | 12.00 | 63.81 | 2.42 |
| Toremifene | n | 9 | 9 | 9 | 9 | 9 |
| | stat | n.s. | ** | ** | ** | ** |
| Orx | mean | 3.02 | 0.34 | 4.78 | 21.26 | 2.07 |
| 10 mg/kg/d | SD | 1.93 | 0.33 | 5.04 | 22.22 | 2.54 |
| Toremifene | n | 9 | 9 | 9 | 9 | 9 |
| | stat | n.s. | ** | ** | ** | ** |
| Orx | mean | 5.31 | 0.43 | 10.63 | 42.70 | 3.13 |
| 0.2 mg/kg/d | SD | 3.00 | 0.36 | 10.69 | 43.79 | 3.12 |
| Estradiol | n | 8 | 8 | 8 | 8 | 8 |
| | stat | n.s. |  |  |  |  | n.a. not applicable;
n.s. not significant;
** p < 0.05 vs. ORX + vehicle

Figure 5:
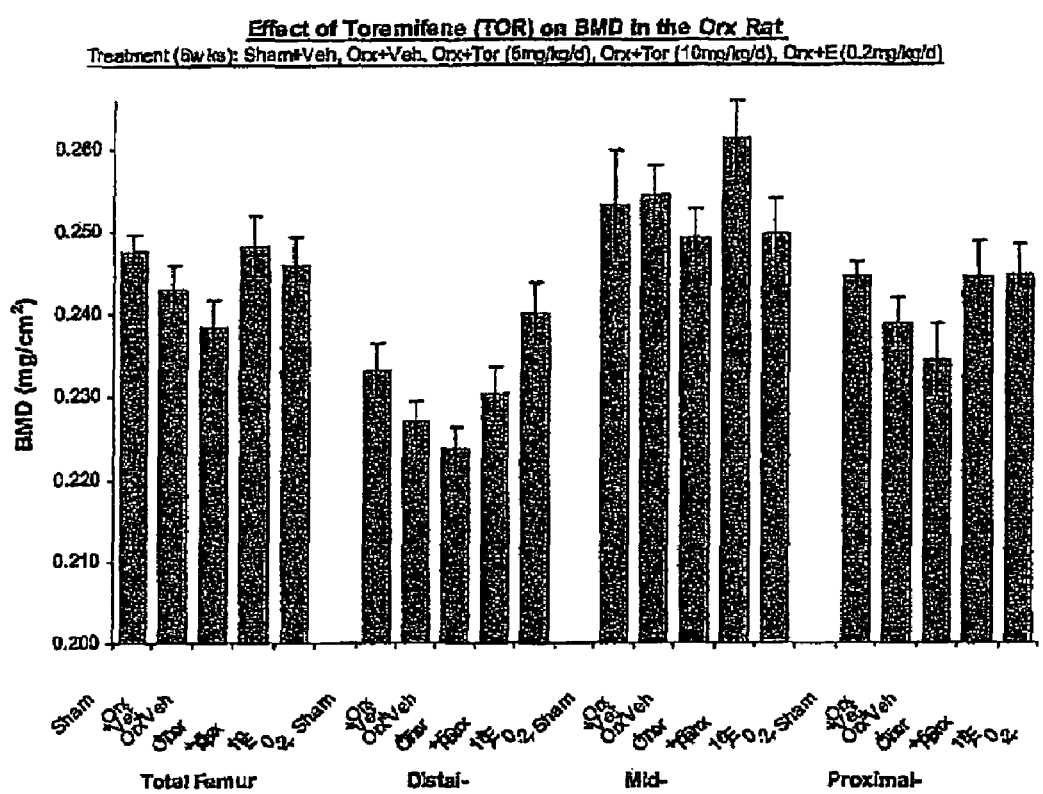
FIG. 5: Effect of Toremifene on BMD in the ORX Rat.

Bone Mineral Density (BMD) of Femur: After 6 weeks of treatment, excised femurs were subjected to DXA scan. The scan results were analyzed in four different regions of interest: whole femur, distal femur, midshaft femur and proximal femur. Summarized data is shown in Tables 8a and 8b, and FIG. 5.

For the whole femur, Orx did not alter bone mass to any significant extent and treatment with toremifene or estradiol did not exhibit any significant effect either. The distal femur is a site that is rich in trabecular bone. At the distal femur, Orx increased bone area and as a result decreased bone density. Treatment with 10 mg/kg/d toremifene prevented Orx-related loss of bone density, the action of Tor being due to reduction in bone area. E, on the other hand, increased bone mineral content and thus significantly improved overall density (p<0.05 vs. Orx+Vehicle). The midshaft femur is rich in cortical bone. Like the distal femur, the proximal femur is a trabecular bone rich site. At the proximal femur, Orx resulted in a small loss in bone mineral density. As in distal femur, while 5 mg/kg/d Tor was ineffective, treatment with 10 mg/kg/d Tor and E was somewhat helpful in preventing this loss, the bone density with both treatments being at the level of sham control. Orx did not alter the bone mineral density at the midshaft femur and Tor or E also did not show any effect at this site.

TABLE 8a

BMD of Whole Femur and Distal Femur at 6 wks

| Treatment Group | Data | Whole femur | | | Distal femur | | |
|---|---|---|---|---|---|---|---|
| | | Bone Mineral Content gm | Bone Area $cm^2$ | Bone Mineral Density $gm/cm^2$ | Bone Mineral Content gm | Bone Area $cm^2$ | Bone Mineral Density $gm/cm^2$ |
| Sham vehicle | mean | 0.588 | 2.392 | 0.245 | 0.154 | 0.662 | 0.233 |
| | SD | 0.073 | 0.253 | 0.008 | 0.012 | 0.057 | 0.009 |
| | n | 8 | 8 | 8 | 8 | 8 | 8 |
| | stat | n.a. | n.a. | n.a. | n.a. | n.a. | n.a. |
| ORX vehicle | mean | 0.614 | 2.525 | 0.243 | 0.154 | 0.678 | 0.227 |
| | SD | 0.028 | 0.090 | 0.008 | 0.007 | 0.023 | 0.007 |
| | n | 8 | 8 | 8 | 8 | 8 | 8 |
| | stat | n.s. | n.s. | n.s. | n.s. | n.s. | n.s. |
| ORX 5 mg/kg/d Toremifene | mean | 0.570 | 2.389 | 0.238 | 0.145 | 0.649 | 0.224 |
| | SD | 0.043 | 0.101 | 0.010 | 0.009 | 0.025 | 0.008 |
| | n | 9 | 9 | 9 | 9 | 9 | 9 |
| | stat | n.s. | n.s. | n.s. | n.s. | n.s. | n.s. |
| ORX 10 mg/kg/d Toremifene | mean | 0.601 | 2.420 | 0.248 | 0.152 | 0.659 | 0.230 |
| | SD | 0.045 | 0.124 | 0.011 | 0.012 | 0.036 | 0.010 |
| | n | 9 | 9 | 9 | 9 | 9 | 9 |
| | stat | n.s. | n.s. | n.s. | n.s. | n.s. | n.s. |
| ORX 0.2 mg/kg/d Estradiol | mean | 0.609 | 2.480 | 0.246 | 0.162 | 0.674 | 0.240 |
| | SD | 0.033 | 0.093 | 0.010 | 0.009 | 0.022 | 0.010 |
| | n | 8 | 8 | 8 | 8 | 8 | 8 |
| | stat | n.s. | n.s. | n.s. | n.s. | n.s. | ** | n.a. not applicable;
n.s. not siginificant;
** $p < 0.05$ vs. Orx + vehicle

TABLE 8b

BMD of Midshaft Femur and Proximal Femur at 6 wks

| Treatment Group | Data | Midshaft femur | | | Proximal femur | | |
|---|---|---|---|---|---|---|---|
| | | Bone Mineral Content gm | Bone Area $cm^2$ | Bone Mineral Density $gm/cm^2$ | Bone Mineral Content gm | Bone Area $cm^2$ | Bone Mineral Density $gm/cm^2$ |
| Sham vehicle | mean | 0.283 | 1.114 | 0.253 | 0.151 | 0.618 | 0.244 |
| | SD | 0.037 | 0.087 | 0.019 | 0.031 | 0.128 | 0.005 |
| | n | 8 | 8 | 8 | 8 | 8 | 8 |
| | stat | n.a. | n.a. | n.a. | n.a. | n.a. | n.a. |
| ORX vehicle | mean | 0.295 | 1.160 | 0.254 | 0.166 | 0.697 | 0.239 |
| | SD | 0.016 | 0.054 | 0.010 | 0.008 | 0.030 | 0.009 |
| | n | 8 | 8 | 8 | 8 | 8 | 8 |
| | stat | n.s. | n.s. | n.s. | n.s. | n.s. | n.s. |
| ORX 5 mg/kg/d Toremifene | mean | 0.271 | 1.086 | 0.249 | 0.154 | 0.658 | 0.234 |
| | SD | 0.023 | 0.055 | 0.011 | 0.014 | 0.038 | 0.013 |
| | n | 9 | 9 | 9 | 9 | 9 | 9 |
| | stat | n.s. | n.s. | n.s. | n.s. | n.s. | n.s. |
| ORX 10 mg/kg/d Toremifene | mean | 0.286 | 1.094 | 0.261 | 0.164 | 0.672 | 0.244 |
| | SD | 0.025 | 0.065 | 0.014 | 0.012 | 0.034 | 0.013 |
| | n | 9 | 9 | 9 | 9 | 9 | 9 |
| | stat | n.s. | n.s. | n.s. | n.s. | n.s. | n.s. |
| ORX 0.2 mg/kg/d Estradiol | mean | 0.281 | 1.128 | 0.250 | 0.167 | 0.685 | 0.245 |
| | SD | 0.016 | 0.049 | 0.013 | 0.009 | 0.025 | 0.011 |
| | n | 8 | 8 | 8 | 8 | 8 | 8 |
| | stat | n.s. | n.s. | n.s. | n.s. | n.s. | n.s. | n.a. not applicable;
n.s. not significant;
** $p < 0.05$ vs. Orx + vehicle

Measurement of Bone Mechanical Properties

A) Compression Test of the Distal Femur

A segment of the distal femur was subject to a compression test. Unexpectedly, ORX animals displayed better bone strength than Sham-operated animals at Week 6. At Week 6, Toremifene treatment resulted in bone strength similar to that of Sham-operated animals and estradiol treatment had the highest values in all groups. At Week 12, there was little difference between ORX and Sham-operated animals. Treatment with 5 mg/kg/d of Toremifene maintained similar strength, while there was a small decrease in strength in the 10 mg/kg/d Toremifene-treated group. Estradiol treatment, once again, had the highest values at Week 12, similar to Week 6. No statistically significant difference was evident in any of the treatment groups. Summarized data is shown in Tables 9a-9b.

There were no discernable differences in bone strength in any of the treatment groups at the femoral shaft. Summarized data is shown in Table 10.

TABLE 9a

Compression Test of the Distal Femur Collected at Week 6

| Treatment Group | Time Point weeks | | Maximum Load N | Stiffness N/mm | Energy mJ | Ultimate Strength $N/mm^2$ | Elastic Modulus MPa | Toughness $MJ/m^3$ |
|---|---|---|---|---|---|---|---|---|
| Sham vehicle | 6 | mean | 457.46 | 3389.51 | 58.44 | 18.93 | 417.60 | 0.83 |
| | | SD | 71.82 | 935.44 | 16.28 | 3.52 | 135.35 | 0.29 |
| | | n | 8 | 8 | 8 | 8 | 8 | 8 |
| | | stat | n.s. | n.s. | n.s. | n.s. | ** | n.s. |
| ORX vehicle | 6 | mean | 537.44 | 4207.28 | 61.19 | 24.67 | 586.71 | 0.92 |
| | | SD | 136.73 | 916.23 | 24.77 | 8.34 | 158.48 | 0.45 |
| | | n | 8 | 8 | 8 | 8 | 8 | 8 |
| | | stat | n.a. | n.a. | n.a. | n.a. | n.a. | n.a. |
| ORX 5 mg/kg/d Toremifene | 6 | mean | 469.64 | 4058.07 | 56.00 | 20.54 | 535.08 | 0.81 |
| | | SD | 104.65 | 717.34 | 19.13 | 5.87 | 114.01 | 0.31 |
| | | n | 9 | 9 | 9 | 9 | 9 | 9 |
| | | stat | n.s. | n.s. | n.s. | n.s. | n.s. | n.s. |
| ORX 10 mg/kg/d Toremifene | 6 | mean | 447.29 | 3549.70 | 66.19 | 18.47 | 440.77 | 0.91 |
| | | SD | 103.70 | 600.42 | 22.66 | 4.49 | 65.73 | 0.32 |
| | | n | 9 | 9 | 9 | 9 | 9 | 9 |
| | | stat | n.s. | n.s. | n.s. | n.s. | n.s. | n.s. |
| ORX 0.2 mg/kg/d Estradiol | 6 | mean | 561.45 | 4758.55 | 66.00 | 22.89 | 579.48 | 0.91 |
| | | SD | 107.68 | 688.47 | 18.57 | 5.41 | 126.28 | 0.30 |
| | | n | 8 | 8 | 8 | 8 | 8 | 8 |
| | | stat | n.s. | n.s. | n.s. | n.s. | n.s. | n.s. | n.a. not applicable;
n.s. not significant;
** $p < 0.05$ vs. ORX + vehicle

TABLE 9b

Compression Test of the Distal Femur Collected at Week 12

| Treatment Group | Time Point weeks | | Maximum Load N | Stiffness N/mm | Energy mJ | Ultimate Strength $N/mm^2$ | Elastic Modulus MPa | Toughness $MJ/m^3$ |
|---|---|---|---|---|---|---|---|---|
| Sham vehicle | 12 | mean | 447.89 | 3804.83 | 54.10 | 18.18 | 469.64 | 0.73 |
| | | SD | 56.11 | 1063.77 | 21.97 | 2.75 | 146.22 | 0.28 |
| | | n | 6 | 6 | 6 | 6 | 6 | 6 |
| | | stat | n.s. | n.s. | n.s. | n.s. | n.s. | n.s. |
| ORX vehicle | 12 | mean | 469.46 | 3701.10 | 47.73 | 18.43 | 437.09 | 0.62 |
| | | SD | 131.36 | 1028.90 | 12.57 | 5.78 | 137.44 | 0.16 |
| | | n | 10 | 10 | 10 | 10 | 10 | 10 |
| | | stat | n.a. | n.a. | n.a. | n.a | n.a. | n.a. |
| ORX 5 mg/kg/d Toremifene | 12 | mean | 458.79 | 3175.07 | 53.13 | 18.09 | 379.32 | 0.69 |
| | | SD | 123.60 | 1367.19 | 17.22 | 4.76 | 164.22 | 0.20 |
| | | n | 10 | 10 | 10 | 10 | 10 | 10 |
| | | stat | n.s. | n.s. | n.s. | n.s. | n.s. | n.s. |
| ORX 10 mg/kg/d Toremifene | 12 | mean | 411.45 | 3366.63 | 45.57 | 16.81 | 418.05 | 0.62 |
| | | SD | 152.71 | 1438.59 | 14.91 | 6.06 | 193.28 | 0.19 |
| | | n | 10 | 10 | 10 | 10 | 10 | 10 |
| | | stat | n.s. | n.s. | n.s. | n.s. | n.s. | n.s. |
| ORX 0.2 mg/kg/d Estradiol | 12 | mean | 487.94 | 3714.71 | 55.94 | 20.66 | 473.02 | 0.78 |
| | | SD | 206.15 | 1521.39 | 19.74 | 8.82 | 189.11 | 0.29 |
| | | n | 10 | 10 | 10 | 10 | 10 | 10 |
| | | stat | n.s. | n.s. | n.s. | n.s. | n.s. | n.s. | n.a. not applicable;
n.s. not significant;
** $p < 0.05$ vs. ORX + vehicle

B) Three Point Bending Test of the Femoral Shaft

TABLE 10

Three Point Bending Test of the Femoral Shaft

| Treatment Group | Time Point weeks | | Maximum Load N | Stiffness N/mm | Energy mJ | Ultimate Strength N/mm² | Elastic Modulus MPa | Toughness MJ/m³ |
| --- | --- | --- | --- | --- | --- | --- | --- | --- |
| Sham vehicle | 12 | mean | 297.14 | 882.11 | 107.20 | 164.11 | 4006.27 | 7.13 |
| | | SD | 35.58 | 245.21 | 16.72 | 11.46 | 878.02 | 0.87 |
| | | n | 6 | 6 | 6 | 6 | 6 | 6 |
| | | stat | n.s. | n.s. | n.s. | n.s. | n.s. | n.s. |
| ORX vehicle | 12 | mean | 279.68 | 1048.31 | 90.07 | 149.74 | 4686.32 | 5.79 |
| | | SD | 21.99 | 61.93 | 11.96 | 12.80 | 586.19 | 0.72 |
| | | n | 10 | 10 | 10 | 10 | 10 | 10 |
| | | stat | n.a. | n.a. | n.a | n.a. | n.a. | n.a. |
| ORX 5 mg/kg/d Toremifene | 12 | mean | 263.54 | 944.78 | 83.40 | 150.45 | 4505.90 | 5.67 |
| | | SD | 17.77 | 188.45 | 14.61 | 11.21 | 713.56 | 1.06 |
| | | n | 10 | 10 | 10 | 10 | 10 | 10 |
| | | stat | n.s. | n.s. | n.s. | n.s. | n.s. | n.s. |
| ORX 10 mg/kg/d Toremifene | 12 | mean | 272.56 | 910.47 | 88.58 | 161.23 | 4557.46 | 6.16 |
| | | SD | 26.44 | 194.37 | 19.20 | 18.63 | 762.38 | 1.47 |
| | | n | 10 | 10 | 10 | 10 | 10 | 10 |
| | | stat | n.s. | n.s. | n.s. | n.s. | n.s. | n.s. |
| ORX 0.2 mg/kg/d Estradiol | 12 | mean | 287.22 | 986.71 | 98.61 | 172.51 | 5149.41 | 6.85 |
| | | SD | 35.41 | 87.54 | 17.64 | 13.74 | 691.15 | 0.89 |
| | | n | 10 | 10 | 10 | 10 | 10 | 10 |
| | | stat | n.s. | n.s | n.s | ** | n.s. | n.s. | n.a. not applicable;
n.s. not significant;
** p < 0.05 vs. ORX + vehicle

C) Compression Test of the Vertebral Body

ORX induced decreases in bone strength, when compared to Sham-operated animals. Toremifene treatment did not prevent these changes and, in fact, it may have worsened the changes at the 10 mg/kg/d dose. Estradiol treatment prevented loss of bone strength due to ORX. Summarized data is shown in Table 11.

TABLE 11

Compression Test of the Vertebral Body

| Treatment Group | Time Point weeks | | Maximum Load N | Stiffness N/mm | Energy mJ | Ultimate Strength N/mm² | Elastic Modulus MPa | Toughness MJ/m³ |
| --- | --- | --- | --- | --- | --- | --- | --- | --- |
| Sham vehicle | 12 | mean | 301.44 | 1280.09 | 65.62 | 24.54 | 419.72 | 1.33 |
| | | SD | 61.99 | 672.88 | 28.80 | 5.64 | 243.51 | 0.51 |
| | | n | 6 | 6 | 6 | 6 | 6 | 6 |
| | | stat | n.s. | n.s. | n.s. | n.s. | n.s. | n.s. |
| ORX vehicle | 12 | mean | 259.91 | 1429.91 | 51.70 | 22.29 | 484.39 | 1.11 |
| | | SD | 35.92 | 260.16 | 30.41 | 3.60 | 103.37 | 0.62 |
| | | n | 10 | 10 | 10 | 10 | 10 | 10 |
| | | stat | n.a. | n.a. | n.a. | n.a. | n.a. | n.a. |
| ORX 5 mg/kg/d Toremifene | 12 | mean | 238.19 | 1391.70 | 36.60 | 19.08 | 446.38 | 0.72 |
| | | SD | 55.49 | 501.31 | 19.46 | 5.22 | 182.57 | 0.31 |
| | | n | 10 | 10 | 10 | 10 | 10 | 10 |
| | | stat | n.s. | n.s. | n.s. | n.s. | n.s. | n.s. |
| ORX 10 mg/kg/d Toremifene | 12 | mean | 206.48 | 1255.47 | 27.02 | 18.12 | 438.64 | 0.59 |
| | | SD | 61.98 | 477.48 | 9.95 | 5.56 | 161.47 | 0.22 |
| | | n | 10 | 10 | 10 | 10 | 10 | 10 |
| | | stat | n.s. | n.s. | ** | n.s. | n.s. | ** |
| ORX 0.2 mg/kg/d Estradiol | 12 | mean | 298.04 | 1648.17 | 43.60 | 25.75 | 589.03 | 0.94 |
| | | SD | 87.59 | 809.16 | 16.45 | 8.75 | 356.36 | 0.36 |
| | | n | 10 | 10 | 10 | 10 | 10 | 10 |
| | | stat | n.s. | n.s. | n.s. | n.s. | n.s. | n.s. | n.a. not applicable;
n.s. not significant;
** p < 0.05 vs. ORX + vehicle

D) Cantilever Compression Test of the Femoral Neck

There were no changes in bone strength at the femoral neck in any of the treatment groups. Summarized data is shown in Table 12.

TABLE 12

Cantilever Compression Test of the Femoral Neck

| Time | Maximum |

| Treatment Group | Point weeks | | Load N | Stiffness N/mm | Energy mJ |
|---|---|---|---|---|---|
| Sham vehicle | 12 | mean | 113.50 | 198.48 | 50.67 |
| | | SD | 9.06 | 81.99 | 7.51 |
| | | n | 6 | 6 | 6 |
| | | stat | n.s. | n.s. | n.s. |
| ORX vehicle | 12 | mean | 117.83 | 204.06 | 46.50 |
| | | SD | 21.18 | 53.10 | 19.03 |
| | | n | 10 | 10 | 10 |
| | | stat | n.a. | n.a. | n.a. |
| ORX 5 mg/kg/d Toremifene | 12 | mean | 116.46 | 211.77 | 46.53 |
| | | SD | 16.01 | 45.26 | 16.32 |
| | | n | 10 | 10 | 10 |
| | | stat | n.s. | n.s. | n.s. |
| ORX 10 mg/kg/d Toremifene | 12 | mean | 117.50 | 211.73 | 44.59 |
| | | SD | 18.16 | 52.67 | 13.90 |
| | | n | 10 | 10 | 10 |
| | | stat | n.s. | n.s. | n.s. |
| ORX 0.2 mg/kg/d Estradiol | 12 | mean | 114.96 | 209.95 | 40.07 |
| | | SD | 18.16 | 49.00 | 12.37 |
| | | n | 10 | 10 | 10 |
| | | stat | n.s. | n.s. | n.s. | n.a. not applicable;
n.s. not significant;
** $p < 0.05$ vs. ORX + vehicle

SUMMARY

The efficacy of a SERM, Toremifene, in preventing bone loss was tested in a model of male osteoporosis, orchidectomized rats. Two doses of Toremifene, 5 and 10 mg/kg/d, and a comparator, estradiol at 0.2 mg/kg/d, were used to treat orchidectomized rats. Various skeletal sites were examined after 6 or 12 weeks of treatment. Bone mass, strength, microarchitecture by histomorphometry and ash density were used to determine changes in bone.

Orchidectomy induced a significantly elevated bone turnover state, as seen in increased osteoclasts and bone formation rate, at both the proximal tibia and lumbar vertebral body. As a result, there were reductions in bone mass at the distal femur, in trabecular bone volume at the proximal tibia and lumbar vertebral body and in strength parameters at the lumbar vertebral body, however, none of these changes reached statistically significant levels.

Toremifene at either 5 or 10 mg/kg/d significantly reduced the ochidectomy-induced elevation in bone turnover, with results similar to treatment with 0.2 mg/kg/d of estradiol. Whereas Toremifene treatment was able to fully prevent the loss of trabecular bone volume, its effects on bone mass and strength were not as uniform. Treatment with 5 mg/kg/d of Toremifene consistently exhibited similar or better values than vehicle-treated animals, but treatment with 10 mg/kg/d of Toremifene displayed occasional reductions in bone mass and strength parameters. Estradiol treatment showed improved bone mass, microarchitecture and strength parameters at each of the bone sites tested.

In conclusion, Toremifene treatment induced a significant reduction in orchidectomy-induced elevations of bone turnover. Toremifene performed well in preventing trabecular bone-loss, but its effect on cortical bone is less uniform. This demonstrates that Toremifene could be used in the treatment of male osteoporosis.

What is claimed is:

1. A method of treating androgen-deprivation induced osteoporosis in a male subject suffering from prostate cancer, said method comprising the step of administering to said subject a Selective Estrogen Receptor Modulator (SERM) or its isomer, pharmaceutically acceptable salt, pharmaceutical product, hydrate, N-oxide, or any combination thereof wherein said SERM is administered at a dosage of about 20 mg per day to about 80 per day.

2. A method of treating androgen-deprivation induced osteoporosis in a male subject suffering from prostate cancer, said method comprising the step of administering to said subject a Selective Estrogen Receptor Modulator (SERM) or its isomer, pharmaceutically acceptable salt, pharmaceutical product, hydrate, N-oxide, or any combination thereof wherein said SERM is administered at a dosage of 20 mg per day.

3. A method of treating androgen-deprivation induced osteoporosis in a male subject suffering from prostate cancer, said method comprising the step of administering to said subject a Selective Estrogen Receptor Modulator (SERM) or its isomer, pharmaceutically acceptable salt, pharmaceutical product, hydrate, N-oxide, or any combination thereof wherein said SERM is administered at a dosage of 40 mg per day.

4. A method of treating androgen-deprivation induced osteoporosis in a male subject suffering from prostate cancer, said method comprising the step of administering to said subject a Selective Estrogen Receptor Modulator (SERM) or its isomer, pharmaceutically acceptable salt, pharmaceutical product, hydrate, N-oxide, or any combination thereof wherein said SERM is administered at a dosage of 60 mg per day.

5. A method of treating androgen-deprivation induced osteoporosis in a male subject suffering from prostate cancer, said method comprising the step of administering to said subject a Selective Estrogen Receptor Modulator (SERM) or its isomer, pharmaceutically acceptable salt, pharmaceutical product, hydrate, N-oxide, or any combination thereof wherein said SERM is administered at a dosage of 80 mg per day.

6. A method of treating androgen-deprivation induced osteoporosis in a male subject suffering from prostate cancer, said method comprising the step of administering to said subject a Selective Estrogen Receptor Modulator (SERM) or its isomer, pharmaceutically acceptable salt, pharmaceutical product, hydrate, N-oxide, or any combination thereof wherein said SERM is Toremifene and is administered at a dosage of about 20 mg per day to about 80 mg per day.

7. A method of treating androgen-deprivation induced osteoporosis in a male subject suffering from prostate cancer, said method comprising the step of administering to said subject a Selective Estrogen Receptor Modulator (SERM) or its isomer, pharmaceutically acceptable salt, pharmaceutical product, hydrate, N-oxide, or any combination thereof wherein said SERM is Toremifene and is administered at a dosage of 20 mg per day.

8. A method of treating androgen-deprivation induced osteoporosis in a male subject suffering from prostate cancer, said method comprising the step of administering to said subject a Selective Estrogen Receptor Modulator (SERM) or its isomer, pharmaceutically acceptable salt, pharmaceutical product, hydrate, N-oxide, or any combination thereof wherein said SERM is Toremifene and is administered at a dosage of 40 mg per day.

9. A method of treating androgen-deprivation induced osteoporosis in a male subject suffering from prostate cancer, said method comprising the step of administering to said subject a Selective Estrogen Receptor Modulator (SERM) or its isomer, pharmaceutically acceptable salt, pharmaceutical product, hydrate, N-oxide, or any combination thereof wherein said SERM is Toremifene and is administered at a dosage of 60 mg per day.

10. A method of treating androgen-deprivation induced osteoporosis in a male subject suffering from prostate cancer, said method comprising the step of administering to said subject a Selective Estrogen Receptor Modulator (SERM) or its isomer, pharmaceutically acceptable salt, pharmaceutical product, hydrate, N-oxide, or any combination thereof wherein said SERM is Toremifene and is administered at a dosage of 80 mg per day.

11. A method of suppressing, inhibiting or reducing the risk of developing androgen-deprivation induced osteoporosis in a male subject suffering from prostate cancer, said method comprising the step of administering to said subject a SERM or its isomer, pharmaceutically acceptable salt, pharmaceutical product, hydrate, N-oxide, or any combination thereof wherein said SERM is administered at a dosage of about 20 mg per day to about 80 mg per day.

12. A method of suppressing, inhibiting or reducing the risk of developing androgen-deprivation induced osteoporosis in a male subject suffering from prostate cancer, said method comprising the step of administering to said subject a SERM or its isomer, pharmaceutically acceptable salt, pharmaceutical product, hydrate, N-oxide, or any combination thereof wherein said SERM is administered at a dosage of 20 mg per day.

13. A method of suppressing, inhibiting or reducing the risk of developing androgen-deprivation induced osteoporosis in a male subject suffering from prostate cancer, said method comprising the step of administering to said subject a SERM or its isomer, pharmaceutically acceptable salt, pharmaceutical product, hydrate, N-oxide, or any combination thereof wherein said SERM is administered at a dosage of 40 mg per day.

14. A method of suppressing, inhibiting or reducing the risk of developing androgen-deprivation induced osteoporosis in a male subject suffering from prostate cancer, said method comprising the step of administering to said subject a SERM or its isomer, pharmaceutically acceptable salt, pharmaceutical product, hydrate, N-oxide, or any combination thereof wherein said SERM is administered at a dosage of 60 mg per day.

15. A method of suppressing, inhibiting or reducing the risk of developing androgen-deprivation induced osteoporosis in a male subject suffering from prostate cancer, said method comprising the step of administering to said subject a SERM or its isomer, pharmaceutically acceptable salt, pharmaceutical product, hydrate, N-oxide, or any combination thereof wherein said SERM is administered at a dosage of 80 mg per day.

16. A method of suppressing, inhibiting or reducing the risk of developing androgen-deprivation induced osteoporosis in a male subject suffering from prostate cancer, said method comprising the step of administering to said subject a SERM or its isomer, pharmaceutically acceptable salt, pharmaceutical product, hydrate, N-oxide, or any combination thereof wherein said SERM is Toremifene and is administered at a dosage of about 20 mg per day to about 80 mg per day.

17. A method of suppressing, inhibiting or reducing the risk of developing androgen-deprivation induced osteoporosis in a male subject suffering from prostate cancer, said method comprising the step of administering to said subject a SERM or its isomer, pharmaceutically acceptable salt, pharmaceutical product, hydrate, N-oxide, or any combination thereof wherein said SERM is Toremifene and is administered at a dosage of 20 mg per day.

18. A method of suppressing, inhibiting or reducing the risk of developing androgen-deprivation induced osteoporosis in a male subject suffering from prostate cancer, said method comprising the step of administering to said subject a SERM or its isomer, pharmaceutically acceptable salt, pharmaceutical product, hydrate, N-oxide, or any combination thereof wherein said SERM is Toremifene and is administered at a dosage of 40 mg per day.

19. A method of suppressing, inhibiting or reducing the risk of developing androgen-deprivation induced osteoporosis in a male subject suffering from prostate cancer, said method comprising the step of administering to said subject a SERM or its isomer, pharmaceutically acceptable salt, pharmaceutical product, hydrate, N-oxide, or any combination thereof wherein said SERM is Toremifene and is administered at a dosage of 60 mg per day.

20. A method of suppressing, inhibiting or reducing the risk of developing androgen-deprivation induced osteoporosis in a male subject suffering from prostate cancer, said method comprising the step of administering to said subject a SERM or its isomer, pharmaceutically acceptable salt, pharmaceutical product, hydrate, N-oxide, or any combination thereof wherein said SERM is Toremifene and is administered at a dosage of 80 mg per day.

21. A method of treating androgen-deprivation induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of about 20 mg per day to about 80 mg per day.

22. A method of treating androgen-deprivation induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 20 mg per day.

23. A method of treating androgen-deprivation induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 40 mg per day.

24. A method of treating androgen-deprivation induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 60 mg per day.

25. A method of treating androgen-deprivation induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 80 mg per day.

26. A method of treating androgen-deprivation induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of about 20 mg per day to about 80 mg per day.

27. A method of treating androgen-deprivation induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 20 mg per day.

28. A method of treating androgen-deprivation induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 40 mg per day.

29. A method of treating androgen-deprivation induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 60 mg per day.

30. A method of treating androgen-deprivation induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 80 mg per day.

31. A method of suppressing, inhibiting or reducing the risk of developing androgen deprivation-induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of about 20 mg per day to about 80 mg per day.

32. A method of suppressing, inhibiting or reducing the risk of developing androgen deprivation-induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 20 mg per day.

33. A method of suppressing, inhibiting or reducing the risk of developing androgen deprivation-induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 40 mg per day.

34. A method of suppressing, inhibiting or reducing the risk of developing androgen deprivation-induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 60 mg per day.

35. A method of suppressing, inhibiting or reducing the risk of developing androgen deprivation-induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 80 mg per day.

36. A method of suppressing, inhibiting or reducing the risk of developing androgen deprivation-induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of about 20 mg per day to about 80 mg per day.

37. A method of suppressing, inhibiting or reducing the risk of developing androgen deprivation-induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 20 mg per day.

38. A method of suppressing, inhibiting or reducing the risk of developing androgen deprivation-induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 40 mg per day.

39. A method of suppressing, inhibiting or reducing the risk of developing androgen deprivation-induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 60 mg per day.

40. A method of suppressing, inhibiting or reducing the risk of developing androgen deprivation-induced loss of bone mineral density (BMD) in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 80 mg per day.

41. A method of treating androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of about 20 mg per day to about 80 mg per day.

42. A method of treating androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 20 mg per day.

43. A method of treating androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 40 mg per day.

44. A method of treating androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 60 mg per day.

45. A method of treating androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 80 mg per day.

46. A method of treating androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of about 20 mg per day to about 80 mg per day.

47. A method of treating androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 20 mg per day.

48. A method of treating androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 40 mg per day.

49. A method of treating androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 60 mg per day.

50. A method of treating androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 80 mg per day.

51. A method of suppressing, inhibiting or reducing the risk of developing androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of about 20 mg per day to about 80 mg per day.

52. A method of suppressing, inhibiting or reducing the risk of developing androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 20 mg per day.

53. A method of suppressing, inhibiting or reducing the risk of developing androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 40 mg per day.

54. A method of suppressing, inhibiting or reducing the risk of developing androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 60 mg per day.

55. A method of suppressing, inhibiting or reducing the risk of developing androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is administered at a dosage of 80 mg per day.

56. A method of suppressing, inhibiting or reducing the risk of developing androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of about 20 mg per day to about 80 mg per day.

57. A method of suppressing, inhibiting or reducing the risk of developing androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 20 mg per day.

58. A method of suppressing, inhibiting or reducing the risk of developing androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 40 mg per day.

59. A method of suppressing, inhibiting or reducing the risk of developing androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 60 mg per day.

60. A method of suppressing, inhibiting or reducing the risk of developing androgen-deprivation induced bone fractures in a male subject suffering from prostate cancer, said method comprising the step of administering to said subject a SERM or its isomer, pharmaceutically acceptable salt, pharmaceutical product, hydrate, N-oxide, or any combination thereof, wherein said SERM is Toremifene and is administered at a dosage of 80 mg per day.

61. The method according to any one of claims 1-60, wherein said administering comprises administering a pharmaceutical composition comprising said SERM or its isomer, pharmaceutically acceptable salt, pharmaceutical product, hydrate, N-oxide, or any combination thereof; and a pharmaceutically acceptable carrier.

62. The method according to claim 61, wherein said administering comprises intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

63. The method according to claim 61 wherein said pharmaceutical composition is a pellet, a tablet, a capsule, a solution, a suspension, an emulsion, an elixir, a gel, a cream, a suppository or a parenteral formulation.

* * * * *